US006576442B1

(12) United States Patent
Lev et al.

(10) Patent No.: US 6,576,442 B1
(45) Date of Patent: Jun. 10, 2003

(54) RDGB PROTEINS AND RELATED PRODUCTS AND METHODS

(75) Inventors: Sima Lev, San Carlos, CA (US); Gregory D. Plowman, San Carlos, CA (US); Joseph Schlessinger, San Carlos, CA (US)

(73) Assignees: Sugen, Inc., South San Francisco, CA (US); New York University Medical Center, New York, NY (US)

( * ) Notice: Subject to any disclaimer, the term of this patent is extended or adjusted under 35 U.S.C. 154(b) by 26 days.

(21) Appl. No.: 09/589,619

(22) Filed: Jun. 7, 2000

Related U.S. Application Data

(62) Division of application No. 08/938,291, filed on Sep. 26, 1997, now Pat. No. 6,117,673
(60) Provisional application No. 60/027,337, filed on Oct. 11, 1996.

(51) Int. Cl.[7] .......................... C12N 15/00; C12N 1/20; C12P 21/06; C07H 21/04
(52) U.S. Cl. ...................... 435/69.1; 530/300; 530/350; 435/252.3; 435/320.1; 536/23.1; 536/23.5
(58) Field of Search .............................. 435/69.1, 252.3, 435/320.1; 530/350, 300; 536/23.1, 23.5

(56) References Cited

FOREIGN PATENT DOCUMENTS

WO    WO 96/18738    6/1996

OTHER PUBLICATIONS

Abe et al., "Molecular Characterization of a Novel Metabotropic Glutamate Receptor mGluR5 Coupled to Inositol Phosphate/Ca.sup.2+ Signal Transduction," J. Biol. Chem. 267(19):13361–13368 (1992).
Andrade et al., "A G Protein Couples Serotonin and GABA.sub.B Receptors to the Same Channels in Hippocampus," Science 234:1261–1265 (1986).
Baudy, "Agents for the Treatment of Neurodegenerative Diseases: Part 2" Expert Opin. Ther. Pat. 4(4): 343–378 (1994).
Birnstiel et al., "Adenosine–Mediated Synaptic Inhibition: Partial Blockade by Barium Does Not Prevent Anti–Epileptiform Activity," Synapse 11:191–196 (1992).
Carmeliet, "Ion Channel Agonists: Expectations for Therapy," European Heart Journal 12(Supplement F):30–37 (1991).
Coleman et al., "Protection Against Dendrotoxin–induced Clonic Seizures in Mice by Anitconvulsant Drugs" Brain Research, 575:138–142 (1992).
Cromakalim, "Drugs of the Future" Drugs Future, 17(3) 237–239 (1992).
Dasheiff, "A New Method of Monitoring Membrane Potential in Rat Hippocampal Slices Using Cyanine Voltage–Sensitive Dyes" J. Neurosci. Methods, 13:199–212 (1985).

Fischer, et al. "Neurotransmitters and Epilepsy" *John Wiley & Sons , Inc., NY, NY*, vol. 11 (1991) (Table of Contents only).
Fry et al., "New Insights into Protein–tyrosine Kinase Receptor Signaling Complexes," Protein Science 2:1785–1797 (1993).
Gehlert et al., "ATP Sensitive Potassium Channels: Potential Drug Targets in Neuropsychopharmacology," Prog. Neuro–Psychopharmacol. & Biol. Psychiatry 18:1093–1102 (1994).
Jansen et al., "Immunotoxins: Hybrid Molecules Combining High Specificity and Potent Cytotoxicity," Immunological Rev. 62:185–216 (1982).
Killen, et al *J. Immunology* 133:1335–2549 (1984) (Table of Contents only).
McLean et al., "Oxcarbazepine: Mechanisms of Action," Epilepsia 35:S5–S9 (1994).
Millauer et al., "Glioblastoma Growth Inhibited in Vivo by a Dominant–negative Flk–1 Mutant," Nature 367:576–579 (1994).
Murphy et al., "ATP–sensitive Potassium Channels Counteract Anoxia in Neurones of the Substantia Nigra," Exp. Brain Res. 84:355–358 (1991).
Murphy et al., "Neuronal Selectivity of ATP–Sensitive Potassium Channels in Guinea–Pig Substantia Nigra Revealed by Responses to Anoxia,", J. Physiol. 453:167–183 (1992).
Nelson, "Detection of Acridinium Esters by Chemiluminescence," Nonisotopic DNA Probe Techniques, ed. Larry J. Kricka, (San Diego: Academic Press, Inc.) pp. 275–310 (1992).
Olpe et al., "4–Aminopyridine and Barium Chloride Attenuate the Anti–Epileptic Effect of Carbamazepine in Hippocampal Slices" Experientia, 47(3), 254–257 (1991).
Ping–Su, "Delineating Biochemical and Functional Properties of Sigma Receptors: Emerging Concepts" Crit. Rev. Neurobiol. 7:(3/4):187–203 (1993).
Popoli et al., "Cromakalim (BRL 34915) Counteracts the Epileptiform Acitivity Elicited by Diltiazem and Verapamil in Rats" Br. J. Pharmacol, 104:907–913 (1991).

(List continued on next page.)

*Primary Examiner*—Tekchand Saidha
(74) *Attorney, Agent, or Firm*—Beth A. Burrous; Foley & Lardner

(57) ABSTRACT

The present invention features a method for treatment of an organism having a disease or condition characterized by an abnormality in a signal transduction pathway, wherein the signal transduction pathway includes a rdgB protein. The invention also features methods for diagnosing such diseases and for screening for agents that will be useful in treating such diseases. The invention also features purified and/or isolated nucleic acid encoding a rdgB protein.

13 Claims, 1 Drawing Sheet

OTHER PUBLICATIONS

Porter et al., "New Antiepileptic Drugs: From Serependipity to Rational Discovery," Epilepsia 33:S1–S6 (1992).

Ricard–Mousnier et al., "Role Des Canaux Ioniques Potentiel–depandents Dans L'epileptogenese," Neurophysiologie Clinique 23:395–421 (1993).

Rubboli et al., "H. Sapiens mRNA for DRES9 protein," EMBL Database—European Bioinformatics Institute, Accession No. X98654, Jun. 30, 1997.

Rubboli et al., "A Mammalian Homologue of the Drosophila Retinal Degeneration B Gene: Implications for the Evolution of Phototransduction Mechanisms," Genes Func. 1:205–213 (1997).

Rutecki, et al. Epilepsia 32:1–2 (1991) (Table of Contents only).

Simon et al., "Potassium Channel Openers Block Seizure Activity In an In–Vitro Model of Epilepsy," Biophys. J. 64:A100 (1993) (abstract).

Treherne et al., "The Regional Distribution of Sulphonylurea Binding Sites in Rat Brain," Neuroscience 40:523–531 (1991).

Vihtelic et al.,"Localization of Drosophila retinal degeneration B, a Membrane–associated Phosphatidylinositol Transfer Protein," J. of Cell Biology 122:1013–1022 (1993).

Vihtelic et al., "Isolation and Characterization of the Drosophila retinal degeneration B (rdgB) Gene" Genetics 127:761–768 (1991).

[Investigative Ophthalmology & Visual Science (1996), vol. 37, No. 3, pp S949. Meeting information: 1996 Annual meeting of the Association for Research in Vision and Ophthalmology, Fort Lauderdale, Fl, Apr. 21–26, 1996].*

* cited by examiner

RDGB PROTEINS AND RELATED PRODUCTS AND METHODS

INTRODUCTION

The present invention relates generally to newly identified rdgB proteins and related products and methods.

BACKGROUND OF THE INVENTION

The following discussion of the background of the invention and references cited therein are not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine phosphatases (TPs) and tyrosine kinases (TKs), including receptor tyrosine kinases and non-receptor tyrosine kinases.

A tyrosine protein kinase named PYK2, is described in U.S. patent application Ser. No. 08/460,626, filed Jun. 2, 1995, which is a continuation-in-part application of U.S. patent application Ser. No. 08/357,642, filed Dec. 15, 1994, both of which are hereby incorporated herein by reference in their entirety including any drawings. PYK2 contains an N-terminal domain, a catalytic domain, two proline-rich regions, potential Src homology 2 (SH2) binding regions, and a region homologous to the focal adhesion targeting domain.

A type of protein found in Drosophila, called Drosophila retinal degeneration B protein(rdgB)is described in Vihtelic et al., *J. of Cell Biology* 122, :1013–1022, 1993. The sequence described in this reference, however, contained a false stop codon sequencing error and thus the authors were not aware that the Drosophila rdgB contains a PYK-2 binding domain. In addition, this sequence was incorrectly identified as a member of the 6-transmembrane domain family of proteins. These rdgB proteins function in many sensory and neuronal cells of the fly and are directly associated with sight in the fly.

The sequence of a genomic clone of a portion of *C. elegans* has been placed on a computer database, and (although unappreciated), this sequence contains an rdgB sequence with introns. Thus, the GENEBANK database contains raw data of the nucleotide sequence of a series of genomic clones of *c. Elegans*. Using portions of the human rdgb sequence, the present invention identifies an open reading frame that has been to this point unrecognized. An rdgB was thus found segregated into 14 exons in two separate cosmids C54C6 (assc. #Z77131) and MO1F1 (assc. #Z46381).

SUMMARY OF THE INVENTION

The present invention relates to rdgB polypeptides, nucleic acids encoding such polypeptides, cells, tissues and animals containing such polypeptides, antibodies to such polypeptides, assays utilizing such polypeptides, and methods relating to all of the foregoing. Such rdgB polypeptides are involved in various signal transduction pathways and thus the present invention provides several agents and methods useful for diagnosing, treating, and preventing various diseases or conditions associated with abnormalities in these pathways.

The present invention is based in part upon the identification and isolation of a series of novel non-receptor tyrosine kinase binding molecules, termed hrdgB1, hrdgB2, and hrdgB3. The full length nucleic acid sequences encoding these proteins are set forth respectively in SEQ ID NO:1, SEQ ID NO:2, and SEQ ID NO:3. The full length amino acid sequences are set forth respectively in SEQ ID NO:4, SEQ ID NO:5, and SEQ ID NO:6. RDGBs are generally comprised of 3 structural domains. The N-terminal PIT domains described herein have approximately 45% amino acid identity to human PPI1 and PPI2. The PIT domains of RDGB2 and RDGB3 (RDGB1 lacks a PIT domain) have approximately 72% identity with each other and approximately 62–65% identity with the drosophila and *C elegans* rdgB's. The full length amino acid sequence for *c. Elagans* is set forth in SEQ ID NO:7 and the full length Drosophila nucleic acid sequence set forth in SEQ ID NO:8, and the full length Drosophila amino acid sequence is set forth in SEQ ID NO:9. The PIT domains of the rdgBs have a conserved putative ATP binding motif similar to that seen in protein kinases.

The second central domain is present in all human rdgbs described herein and has no sequence homology to any other known domain. The three human rgdbs share 43–47% identity over the 600 to 675 amino acid stretch and show 25–35% identity to the invertebrate rdgB's. This large domain contains three subdomains with much higher identity (66–88% in the human rdgbs and 35–75% with the invertebrate rdbgs.) This high level of conservation, especially across such a diverse set of species, suggests an important functional role for these stretches. The N-terminal portion of the central domain is a conserved acidic region of 10 to 15 amino acids comprised almost exclusively of glutamatic and aspartate residues that may function as a calcium binding motif.

The third rdgB domain is particularly unique to these proteins and consists of the C-terminal 343 to 384 residues of the proteins. There is 60–63% identity amongst the human rdgbs and 40–60% with the invertebrate rdgB's. The comparison with the drosophila rdgb is based on the unique knowledge of this domain and its functional significance as described herein. The published sequence contained a framseshift mutation such that the protein was previously thought to terminate less than halfway through this domain. By comparison with the human sequences, the present invention provides a sequence that extends beyond the end of the drosophila sequence to include amino acids 1054–1249.

Within the PYK2 binding domain is a distinct motif with primary sequence homology to the nucleotide binding region of the ras-related GTP-binding proteins. All members of this family (ras, rho, rac, rab, ran) contain a sequence characterized by the conserved hydrophobic-hydrophobic-G-X-K-X-D-hydrophobic amino acid sequence. The G-X-K motif in the rdgBs is at aa 614 (rdgb1), aa898 (rdgb2), aa 983 (rdgb3) and aa 987 (dm). Based on analysis of the three dimensional structure (by X-ray crystalography) of this region from ras and ran, this motif grasps the nucleotide ring of GDP/GTP as part of the molecular "on-off" switch in these proteins. The rdgbs however lack the upstream p-llop or A-box present in these small G-proteins.

RdgB proteins are involved in key signal transduction pathways related to neurotransmitter signaling. This is based in part on the recognition of existence and significance of domains found in rdgB proteins (see FIG. 1). For example, the experiments described herein demonstrate that rdgB proteins contain a PYK2 binding domain. PYK2 is believed to be responsible for regulating neurotransmitter signaling.

The rdgB proteins also contain a PIT domain, which in Drosophila is involved in PI transfer. PI transfer in humans is involved in the recycling of synaptic vesicles. Thus, in view of the roles of the PYK2 binding domain and the PIT domain, rdgB proteins may be useful in the treatment of conditions of nervous system by enhancing or inhibiting such signaling.

Thus, in a first aspect the invention features an isolated, purified, enriched or recombinant nucleic acid encoding a rdgB polypeptide. Preferably such nucleic acid encodes a mammalian rdgB polypeptide, more preferably it encodes a human rdgB polypeptide.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only nucleotide chain present, but does indicate that it is the predominate sequence present (at least 10–20% more than any other nucleotide sequence) and is essentially free (about 90–95% pure at least) of non-nucleotide material naturally associated with it. Therefore, the term does not encompass an isolated chromosome encoding one or more rdgB polypeptides.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased in a useful manner and preferably separate from a sequence library. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "rdgB polypeptide" is meant 9 or more contiguous amino acids set forth in the full length amino acid sequence of SEQ ID NO:4, SEQ ID NO:5, or SEQ ID NO:6. The rdgB polypeptides can be encoded by full-length nucleic acid sequences or any portion of a full-length nucleic acid sequence, so long as a functional activity of the polypeptide is retained. Preferred functional activities include the ability to bind to the N-terminal portion of PYK2. For example, the present invention encompasses deletion mutants isolated domains, and complementary sequences capable of hybridizing to full length rdgB protein under stringent hybridization conditions.

In preferred embodiments, isolated nucleic acid comprises, consists essentially of, or consists of a nucleic acid sequence set forth in the full length nucleic acid sequence SEQ ID NO:1, SEQ ID NO:2, or SEQ ID NO:3 or at least 27, 30, 45, 60 or 90 contiguous nucleotides thereof and the rdgB polypeptide comprises, consists essentially of, or consists of at least 9, 10, 15, 20, 30, 50, 100, 200, or 300 contiguous amino acids of a rdgB polypeptide.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Compositions and probes of the present invention may contain human nucleic acids encoding a rdgB polypeptide but are substantially free of nucleic acid not encoding rdgB polypeptide. The human nucleic acid encoding a rdgB polypeptide is at least 18 contiguous bases of the nucleotide sequence set forth in SEQ. ID NO. 1, SEQ. ID NO. 2, or SEQ. ID NO. 3 and will selectively hybridize to human genomic DNA encoding a rdgB polypeptide, or is complementary to such a sequence. The nucleic acid may be isolated from a natural source by cDNA cloning or subtractive hybridization; the natural source may be blood, semen, and tissue of various organisms including eukaryotes, mammals, birds, fish, plants, gorillas, rhesus monkeys, chimpanzees and humans; and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions.

By "conserved nucleic acid regions", are meant regions present on two or more nucleic acids encoding a rdgB polypeptide, to which a particular nucleic acid sequence can hybridize to under lower stringency conditions. Examples of lower stringency conditions suitable for screening for nucleic acid encoding rdgB polypeptides are provided in Abe, et al. *J. Biol. Chem.*, 19:13361 (1992) (hereby incorporated by reference herein in its entirety, including any drawings). Preferably, conserved regions differ by no more than 7 out of 20 nucleotides.

By "unique nucleic acid region" is meant a sequence present in a full length nucleic acid coding for a rdgB polypeptide that is not present in a sequence coding for any other naturally occurring polypeptide. Such regions preferably comprise 12 or 20 contiguous nucleotides present in the full length nucleic acid encoding a rdgB polypeptide.

The invention also features a nucleic acid probe for the detection of a rdgB polypeptide or nucleic acid encoding a rdgB polypeptide in a sample. The nucleic acid probe contains nucleic acid that will hybridize to at least one sequence set forth in SEQ ID NO:1, SEQ ID NO:2, or SEQ ID NO:3.

In preferred embodiments the nucleic acid probe hybridizes to nucleic acid encoding at least 12, 27, 30, 35, 40, 50, 100, 200, or 300 contiguous amino acids of the full-length sequence set forth in SEQ ID NO:4, SEQ ID NO:5, or SEQ ID NO:6. Various low or high stringency hybridization conditions may be used depending upon the specificity and selectivity desired.

By "high stringency hybridization conditions" is meant those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5× Denhardt's solution, sonicated salmon sperm DNA (50 g/ml), 0.1% SDS, and 10% dextran sulfate at 42° C., with washes at 42° C. in 0.2×SSC and 0.1% SDS. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of rdgB RNA in a sample by contacting the sample with a nucleic acid probe under conditions such that hybridization occurs and detecting the presence or amount of the probe bound to rdgB RNA. The nucleic acid duplex formed between the probe and a nucleic acid sequence coding for a rdgB polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence set forth in SEQ ID NO:1 and a vector or a promoter effective to initiate transcription in a host cell. The recombinant nucleic acid can alternatively contain a transcriptional initiation region functional in a cell, a sequence complimentary to an RNA sequence encoding a rdgB polypeptide and a transcriptional termination region functional in a cell.

In another aspect the invention features an isolated, enriched or purified rdgB polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is the predominate sequence present (at least 10–20% more than any other sequence) and is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired amino acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments rdgB polypeptides contain at least 9, 10, 15, 20, or 30 contiguous amino acids of the full-length sequence set forth in SEQ ID NO:4, SEQ ID NO:5, or SEQ ID NO:6.

In yet another aspect the invention features a purified antibody (e.g., a monoclonal or polyclonal antibody) having specific binding affinity to a rdgB polypeptide. The antibody contains a sequence of amino acids that is able to specifically bind to a rdgB polypeptide.

By "specific binding affinity" is meant that the antibody will bind to a hrgdB polypeptide at a certain detectable amount but will not bind other polypeptides to the same extent, under identical conditions. The present invention also encompasses antibodies that can distinguish hrgdB1 from hrdgB2 or hrdgB3 or can otherwise distinguish between the various rdgBs.

Antibodies having specific binding affinity to a rdgB polypeptide may be used in methods for detecting the presence and/or amount of a rdgB polypeptide is a sample by contacting, the sample with the antibody under conditions such that an immunocomplex forms and detecting the presence and/or amount of the antibody conjugated to the rdgB polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a rdgB polypeptide.

By "hybridoma" is meant an immortalized cell line which is capable of secreting an antibody, for example a rdgB antibody.

In preferred embodiments the rdgB antibody comprises a sequence of amino acids that is able to specifically bind a rdgB polypeptide.

Another aspect of the invention features a method of detecting the presence or amount of a compound capable of binding to a rdgB polypeptide. The method involves incubating the compound with a rdgB polypeptide and detecting the presence or amount of the compound bound to the rdgB polypeptide.

In preferred embodiments, the compound inhibits an activity of rdgB. The present invention also features compounds capable of binding and inhibiting rdgB polypeptide that are identified by methods described above.

In another aspect the invention features a method of screening potential agents useful for treatment of a disease or condition characterized by an abnormality in a signal transduction pathway that contains an interaction between a rdgB polypeptide and a natural binding partner (NBP). The method involves assaying potential agents for those able to promote or disrupt the interaction as an indication of a useful agent.

By "screening" is meant investigating an organism for the presence or absence of a property. The process may include measuring or detecting various properties, including the level of signal transduction and the level of interaction between a rdgB polypeptide and a NBP.

By "disease or condition" is meant a state in an organism, e.g., a human, which is recognized as abnormal by members of the medical community. The disease or condition may be characterized by an abnormality in one or more signal transduction pathways in a cell, preferably a cell listed in table 1, wherein one of the components of the signal transduction pathway is either a rdgB polypeptide or a NBP.

Specific diseases or disorders which might be treated or prevented, based upon the affected cells include: myasthenia gravis; neuroblastoma; disorders caused by neuronal toxins such as cholera toxin, pertusis toxin, or snake venom; acute megakaryocytic myelosis; thrombocytopenia; those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome. Conditions that may be treated by rdgB inhibitors include epilepsy, schizophrenia, extreme hyperactivity in children, chronic pain, and acute pain. Examples of conditions that may be treated by PYK2-rdgB pathway enhancers (for example a phosphatase inhibitor) include stroke, Alzheimer's, Parkinson's, other neurodegenerative diseases and migraine.

Preferred disorders include epilepsy, stroke, schizophrenia, and Parkinson's disorder as there is an established relationship between these disorders and the function of potassium channels. See, McLean et al., *Epilepsia* 35:S5–S9 1994; Ricard-Mousnier et al., *Neurophysiologie Cliniaue* 23:395–421, 1993; *Crit Rev. Veurobiol* 7:187–203, 1994; Simon and Lin, *Biophys. J.* 64:A100, 1993; Birnstiel et al., *Synapse* (NY) 11:191–196, 1992; Coleman et al., *Brain Res.* 575:138–142 1992; Popolip et al., *Br. J. Pharmacol* 104:907–913, 1991; Murphyet al., *Exp. Brain Res.* 84:355–358, 1991; Rutecki et al., *Epilepsia* 32:1–2, 1991; Fisher and Coyle (ed), *Frontiers of Clinical Neurosciene*, Vol. 11 "Neurotransmitters and Epilepsy"; Meeting, Woods Hole Mass., USA IX+260P. John Wiley and Sons, Inc. NY, N.Y.; Treherne and Ashford, *Neuroscience* 40:523–532, 1991; Gehlert, *Prog. Neuro-Psychopharmacol. Biol. Psychiatry* 18:1093–1102, 1994; Baudy, *Expert Opin Ther. Pat.* 1994 4/4:343–378; Porter and Rogawski, *Epilepsia* 33:S1–S6, 1992; Murphy, *J. Physiol.* 453:167–183, 1992; Cromakalim, *Drugs Future* 17/3:237–239, 1992; Carmeliet, *Eur. Heart J.* 12:30–37, 1991; Olpe et al., *Experientia* 47/3:254–257, 1991; Andrade et al., *Science* 234/4781:1261–1265, 1986; Forster, *J. Neurosci. Methods* 13/3–4:199–212, 1985.

In preferred embodiments, the methods described herein involve identifying a patient in need of treatment. Those skilled in the art will recognize that various techniques may be used to identify such patients. For example, cellular potassium levels may be measured or the individuals genes may be examined for a defect.

By "abnormality" is meant an a level which is statistically different from the level observed in organisms not suffering from such a disease or condition and may be characterized as either an excess amount, intensity or duration of signal or a deficient amount, intensity or duration of signal. The abnormality in signal transduction may be realized as an abnormality in cell function, viability or differentiation state. The present invention is based in part on the determination that such abnormality in a pathway can be alleviated by action at the PYK2-rdgB interaction site in the pathway. An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a rdgB polypeptide and PYK2, since the complex formed by such interaction is part of the signal transduction pathway. However, the disease or condition may be characterized by an abnormality in the signal transduction pathway even if the level of interaction between the rdgB polypeptide and NBP is normal.

By "interact" is meant any physical association between polypeptides, whether covalent or non-covalent. This linkage can include many chemical mechanisms, for instance covalent binding, affinity binding, intercalation, coordinate binding and complexation. Examples of non-covalent bonds include electrostatic bonds, hydrogen bonds, and Van der Waals bonds. Furthermore, the interactions between polypeptides may either be direct or indirect. Thus, the association between two given polypeptides may be achieved with an intermediary agent, or several such agents, that connects the two proteins of interest (e.g., a rdgB polypeptide and PYK2). Another example of an indirect interaction is the independent production, stimulation, or inhibition of both a rdgB polypeptide and PYK2 by a regulatory agent. Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above, and also in terms of the distance between the interacting molecules. Indirect interactions may be described in a number of ways, including the number of intermediary agents involved, or the degree of control exercised over the rdgB polypeptide relative to the control exercised over PYK2 or another NBP.

By "disrupt" is meant that the interaction between the rdgB polypeptide and PYK2 or a NBP is reduced either by preventing expression of the rdgB polypeptide, or by preventing expression of PYK2 or NBP, or by specifically preventing interaction of the naturally synthesized proteins or by interfering with the interaction of the proteins.

By "promote" is meant that the interaction between a rdgB polypeptide and PYK2 or NBP is increased either by increasing expression of a rdgB polypeptide, or by increasing expression of PYK2 or a NBP, or by decreasing the dephosphorylating activity of the corresponding regulatory PTP (or other phosphatase acting on other phosphorylated signaling components) by promoting interaction of the rdgB polypeptide and PYK2 or NBP or by prolonging the duration of the interaction. Covalent binding can be promoted either by direct condensation of existing side chains or by the incorporation of external bridging molecules. Many bivalent or polyvalent linking agents are useful in coupling polypeptides, such as an antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, *J. Immunol.* 133:1335–2549; Jansen, F. K., et al., 1982, *Immunological Rev.* 62:185–216; and Vitetta et al., supra).

By "NBP" is meant a natural binding partner of a rdgB polypeptide that naturally associates with a rdgB polypeptide. The structure (primary, secondary, or tertiary) of the particular natural binding partner will influence the particular type of interaction between the rdgB polypeptide and the natural binding partner. For example, if the natural binding partner comprises a sequence of amino acids complementary to the rdgB polypeptide, covalent bonding may be a possible interaction. Similarly, other structural characteristics may allow for other corresponding interactions. The interaction is not limited to particular residues and specifically may involve phosphotyrosine, phosphoserine, or phosphothreonine residues. A broad range of sequences may be capable of interacting with rdgB polypeptides. One example of a natural binding partner may be pyk2, which is described above. Using techniques well known in the art, one may identify several natural binding partners for rdgb polypeptides such as by utilizing a two-hybrid screen.

By "signal transduction pathway" is meant the sequence of events that involves the transmission of a message from an extracellular protein to the cytoplasm through a cell membrane. The signal ultimately will cause the cell to perform a particular function, for example, to uncontrollably proliferate and therefore cause cancer. Various mechanisms for the signal transduction pathway (Fry et al., Protein Science, 2:1785–1797, 1993) provide possible methods for measuring the amount or intensity of a given signal. Depending upon the particular disease associated with the abnormality in a signal transduction pathway, various symptoms may be detected. Those skilled in the art recognize those symptoms that are associated with the various other diseases described herein. Furthermore, since some adapter molecules recruit secondary signal transducer proteins towards the membrane, one measure of signal transduction is the concentration and localization of various proteins and complexes. In addition, conformational changes that are involved in the transmission of a signal may be observed using circular dichroism and fluorescence studies.

In another aspect the invention features a method of diagnosis of an organism for a disease or condition characterized by an abnormality in a signal transduction pathway that contains an interaction between a rdgB polypeptide and PYK2 or a NBP. The method involves detecting the level of interaction as an indication of said disease or condition.

By "organism" is meant any living creature. The term includes mammals, and specifically humans. Preferred organisms include mice, as the ability to treat or diagnose mice is often predictive of the ability to function in other organisms such as humans.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between rdgB polypeptides and PYK2 or NBPs may form the basis to define and diagnose a newly named disease or condition. For example, conventional cancers are classified according to the presence of a particular set of symptoms. However, a subset of these symptoms may both be associated with an abnormality in a particular signalling pathway, such as the ras[21] pathway and in the future these diseases may be reclassified as ras[21] pathway diseases regardless of the particular symptoms observed.

Yet another aspect of the invention features a method for treatment of an organism having a disease or condition characterized by an abnormality in a signal transduction pathway. The signal transduction pathway contains an interaction between a rdgB polypeptide and PYK2 or a NBP and the method involves promoting or disrupting the interaction, including methods that target the rdgB:NBP interaction directly, as well as methods that target other points along the pathway.

By "dominant negative mutant protein" is meant a mutant protein that interferes with the normal signal transduction pathway. The dominant negative mutant protein contains the domain of interest (e.g., an rdgB polypeptide or PYK2 or a NBP), but has a mutation preventing proper signaling, for example by preventing binding of a second domain from the same protein. One example of a dominant negative protein is described in Millauer et al., Nature Feb. 10, 1994. The agent is preferably a peptide which blocks or promotes interaction of the rdgB polypeptide and PYK2 or another NBP. The peptide may be recombinant, purified, or placed in a pharmaceutically acceptable carrier or diluent.

An $EC_{50}$ or $IC_{50}$ of less than or equal to 100 $\mu$M is preferable, and even more preferably less than or equal to 50 $\mu$M, and most preferably less that or equal to 20 $\mu$M. Such lower EC50's or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness. In addition, the molecule may have an $EC_{50}$ or $IC_{50}$ less than or equal to 100 $\mu$M at one or more, but not all cells chosen from the group consisting of parathyroid cell, bone osteoclast, juxtaglomerular kidney cell, proximal tubule kidney cell, distal tubule kidney cell, cell of the thick ascending limb of Henle's loop and/or collecting duct, central nervous system cell, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 nmole and 1 $\mu$mole of the molecule, depending on its $EC_{50}$ or $IC_{50}$ and on the age and size of the patient, and the disease associated with the patient.

In another aspect, the invention describes a polypeptide comprising a recombinant rdgB polypeptide or a unique fragment thereof. By "unique fragment," is meant an amino acid sequence present in a full-length rdgB polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

By "recombinant rdgB polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In another aspect, the invention describes a recombinant cell or tissue containing a purified nucleic acid coding for a rdgB polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the rdgB polypeptide.

In another aspect, the invention features a rdgB polypeptide binding agent able to bind to a rdgB polypeptide. The binding agent is preferably a purified antibody which recognizes an epitope present on a rdgB polypeptide. Other binding agents include molecules which bind to the rdgB polypeptide and analogous molecules which bind to a rdgB polypeptide.

By "purified" in reference to an antibody is meant that the antibody is distinct from naturally occurring antibody, such as in a purified form. Preferably, the antibody is provided as a homogeneous preparation by standard techniques. Uses of antibodies to the cloned polypeptide include those to be used as therapeutics, or as diagnostic tools.

In another aspect, the invention provides a nucleic acid molecule comprising a nucleotide sequence that encodes: (a) a polypeptide having an amino acid sequence set forth in SEQ ID NO:4 from amino acid residues 1–616 or 616–974; (b) the complement of the nucleotide sequence of (a); (c) a polypeptide having an amino acid sequence set forth in SEQ ID NO:5 from amino acid residues 1–250, 250–900, or 900–1243; (d) the complement of the nucleotide sequence of (c); (e) a polypeptide having an amino acid sequence of SEQ ID NO:6 from amino acid residues 1–251, 251–985, or 985–1349; or (f) the complement of the nucleotide sequence of (e). The utility of such isolated domains in the design of protein inhibitors is well-known to those skilled in the art.

The invention also provides an isolated nucleic acid molecule comprising a nucleotide sequence that encodes a polypeptide having the full length amino acid sequence set forth in SEQ ID NO:4; SEQ ID NO:5, or SEQ ID NO:6 except that it lacks at least one, but not more than two, of the domains selected from the group consisting of the, PIT, the central domain, the PYK2 binding domain, the calcium binding domain and the nucleotide binding domain. Such deletion mutants are useful in the design of assays for protein inhibitors. The nucleic acid molecules described above may be, for example, cDNA or genomic DNA and may be placed in a recombinant vector or expression vector. In such a vector, the nucleic acid preferably is operatively associated with the regulatory nucleotide sequence containing transcriptional and translational regulatory information that controls expression of the nucleotide sequence in a host cell.

Thus, the invention also provides a genetically engineered host cell containing any of the nucleotide sequences described herein and the nucleic acid preferably is operatively associated with the regulatory nucleotide sequence containing transcriptional and translational regulatory information that controls expression of the nucleotide sequence in a host cell. Such host cells may obviously be either prokaryotic or eukaryotic.

Other features and advantages of the invention will be apparent from the following description of the preferred embodiments thereof, and from the claims.

DESCRIPTION OF THE PREFERRED EMBODIMENTS

Figure 1:
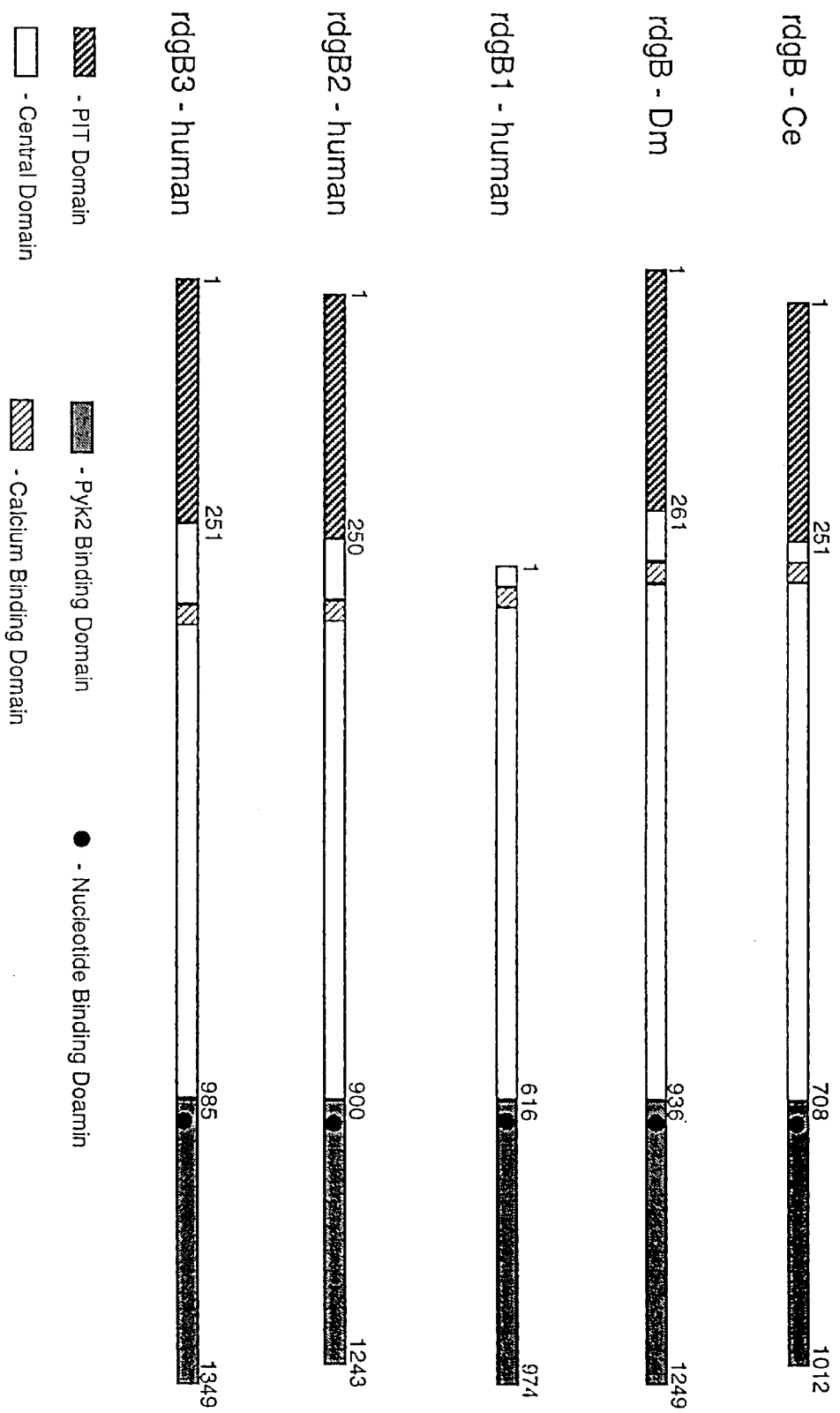
FIG. 1 shows the domains of some preferred full length rdgb proteins.

The present invention relates to rdgB polypeptides, nucleic acids encoding such polypeptides, cells, tissues and animals containing such nucleic acids, antibodies to such polypeptides, assays utilizing such polypeptides, and methods relating to all of the foregoing. Those skilled in the art will recognize that many of the methods described below in relation to rdgB, PYK-2, a NBP, or a complex of rdgB with PYK-2 or a NBP could also be utilized with respect to the other members of this group.

We describe the isolation and characterization of a novel non-receptor tyrosine kinase binding protein, termed rdgB. HrdgB1 is expressed in the brain, spleen, and ovary. HrdgB2 is expressed in many human tissues including brain, heart, thymus, and peripheral blood leukocytes. HrdgB3 is highly expressed in the thymus but is also expressed in the brain, heart, ovary, and testis.

The examples presented for PYK2, supra, reveal a novel mechanism for the coupling, between G-protein coupled receptors and the MAP kinase signaling pathway. These examples also showed that calcium influx induced by membrane depolarization following activation of the nicotinic acetylcholine receptor or other stimuli that cause calcium influx or release from internal stores lead to the activation of PYK2, tyrosine phosphorylation of Shc, recruitment of Grb2/Sos and activation of the MAP kinase signaling pathway. Pyk2 can also link extracellular signals with the JNK/SAP kinase signaling pathway.

RdgB proteins represent a link in the observations discolosed above. RdgB proteins are shown to bind to PYK2 with high affinity both in vitro and in vivo. Evidence of this high affinity interaction is visualized in experiments pulling PYK2 out of a cell lysate with glutathione S-transferase fused rdgB proteins. These experiments are described in the Examples section below. In addition the Drosphila homologs of the rdgB proteins contain a phosphitidylinositol trasferase domain as well as a Ca2+ binding domain. Although the phosphitidyl inositol transferase domain is missing in an alternatively spliced variant, all forms of rdgB proteins contain a Ca2+ binding domain. Thus the Ca2+ binding domain of rdgB proteins are potentially involved in the Ca2+ response observed in PYK2 signaling.

The model presented herein may represent the mechanism underlying calcium mediated regulation of gene expression in neuronal cells induced by MMDA receptor or voltage sensitive calcium channels. The expression pattern of PYK2, the external stimuli that activate the kinase together with its role in the control of MAP kinase and JNK signaling pathways suggests a potential role for PYK2 and rdgB proteins in the control of a broad array of processes in the central nervous system including neuronal plasticity, highly localized control of ion channel function, as well as, localized activation of the MAP kinase and JNK signaling pathways, cell excitability, and synaptic efficacy.

Various other features and aspects of the invention are: Nucleic Acid Encoding A rdgB Polypeptide; A Nucleic Acid Probe for the Detection of RdgB; Probe Based Method And Kit For Detecting RdgB; DNA Constructs Comprising a RdgB Nucleic Acid Molecule and Cells Containing These Constructs; Purified rdgB Polypeptides; RdgB. Antibody And Hybridoma; An Antibody Based Method And Kit For Detecting RdgB; Isolation of Compounds Which Interact With RdgB; Compositions; Disruption of Protein Complexes; Antibodies to Complexes; Pharmaceutical Formulations and Modes of Administration; Identification of Agents; Purification and Production of Complexes; Derivatives of Complexes; and Evaluation of Disorders. All of these aspects and features are explained in detail with respect to PYK-2 in PCT publication WO 96/18738, which is incorporated herein by reference in its entirety, including any drawings. Those skilled in the art will readily appreciate that such description can be easily adapted to rgdB as well, and is equally applicable to the present invention.

EXAMPLES

The examples below are non-limiting and are merely representative of various aspects and features of the procedures used to identify the full-length nucleic and amino acid sequences of a series of rdgB proteins. Experiments demonstrating rdgB expression, interaction and signalling activities are also provided.

Material and Methods

Two Hybrid Screen

The yeast strain L40 containing the reporter genes HIS3 and β-gal under control of upstream LexA-binding site, was used as a host for the two-hybrid screening. PYK2-N terminal domain (aa 2–245), PYKN-ΔI (aa 2–237), PYK-NN (aa2–285) and Fak (aa 2–412) N-terminal domain (aa 2–412) were fused in frame to LexA DNA binding domain. Yeast strain that express the LexA-PYKN fusion protein was transfected with human brain cDNA library (Clontech #HL404AB) fused to GAL4 transcriptional activation domain. Transformants were plated on agar selection medium lacking Uracil (Ura-), Tryptophane (Trp-), Leucine (Leu-) and Histidine (His-). Resulting colonies were isolated and retested for growth on -Ura-Trp-Leu-His plates and for β-galactosidase activity. Plasmid DNA was purified from colonies that were His+, β-gal+ and used for retransformation of yeast strains expressing heterologous baits to determine the specificity of the interaction.

Isolation of rdgBs cDNAs hrdgB1: Human brain, Substania nigra cDNA library (λgt10,Clontoch HL1179a.) was screened with 32-p-labelled probe derived from the yeast prey plasmid encoding GAL10-rdgB1. Four independent clones were isolated, subcloned and analyzed by sequence. Sequence analysis indicated that the 5' end of the gene is missing from our clones. Therefore human fetal brain cDNA library (λgt11, clontech HL3003b) was screened with probe derived from the most 5' region of our new cDNA contig. Sequence analysis of six independent clones that were isolated indicated that all of them are belong to the same gene, hrdgB1, but they are missing the 5' end of the gene. A specific-primed cDNA library was constructed in λZapII utilizing human fetal brain Poly(A)+ RNA as templet for our cDNA synthcasis (Stratagene Kit). 15 independent clones were isolated and allowed subsequently isolation of the full length cDNA of hrdgB1.

hrdgB2 and hrdgB3: A DNA fragment derived from an EST fragment (T12574) was amplified by PCR from human fetal brain cDNA. The PCR product was subcloned, sequenced and used as a probe for screening a human fetal brain cDNA library (λgt11, Clontech H15015b). One positive clone was obtained from this screen. Sequence analysis indicated that it is a partial cDNA clone of a novel gene belongs to the human rdgB family. The cDNA insert of this clone (1.8 kb) was used as a probe for rescreening the same cDNA library. Seven independent clones were obtained, subcloned and sequenced. Sequence analysis indicated that all of them belong to the same gene; hrdgB2, but they are different from the original clone that was isolated from the same library. The 3' end of our first clone (1.8 kb), was used as a probe to screen a human heart cDNA library (Clontech 7759-1, 7760-1) and allowed subsequent isolation two alternative spliced isoforms of hrdgB3.

Northern Blot

Human multiple tissues Northern blots (Clontech HL11296) were hybridized under high-stringency conditions using 32P-labelled cDNA fragment of hrdgB1 (EcoRI-Eco47III nuc# 245–511, hrdgB2 (SacI-Eco47III nuc# 1540–2661) and hrdgB3 Bst-X1 nuc# 912–1472 as probe according to the instructions of the manufacture.

Plasmid Constructs-Two-hybrid Constructs

Fusion with LexA DNA-binding domain: PCR was used to amplified different regions of PYK2 and Fak cDNAs as indicated, the amplified DNA fragments were subcloned into pBTM116 in frame to generate a fusion protein with LexA DNA-binding domain.

Fusion with GAL4 activation domain: PCR was used to amplified different regions of hrdgB1, hrdgB2 or hrdgB3 cDNAs as indicated, the amplified DNA fragments were subcloned into pGAD10 (Clontech) in frame to generate a fusion protein with GAL4 activation domain.

Expression Vectors

The full length cDNAs of hrdgB1, hrdgB2 and hrdgB3 were subcloned into pCMP1 downstream to CMV promoter. An HA-epitope tag (YPYDVPDYAS) SEQ ID NO:10 was fused in frame to their carboxy terminal ends. The PYK2 binding domain of hrdgB2 (residues 911–1243) was subcloned into pCMV-NEO which encode an initiator methionine codon followed by a Myc epitope tag (EQKLISEEDL) SEQ ID NO:1 immediately upstream to the cloning site.

Antibodies

Antibodies against rdgB1 were raised in rabbit immunized either with a synthetic peptide corresponding to amino-acids 965–974 of hrdgB1 (C-Ter Ab), or with a GST-fusion protein containing residues 231–374 (N-Ter Ab) Antibodies against hrdgB2 were raised in rabbit immunized with a synthetic peptide corresponding to amino acids 152–163 of hrdgB2. Antibodies against hrdgB3 were raised in rabbit against MBP-fusion protein containing residues 7–116 of hrdgB3.

EXAMPLE 1

Isolation of Human rdgB Proteins

The yeast two-hybrid system was used to identify proteins that interact with the amino-terminal domain of PYK2. The N-terminal domain of PYK2 was fused to the LexA DNA binding domain and screened a human brain cDNA library. Using a His synthetase gene (HIS3) under the control of LexA operators as a reporter, 124 His+ colonies were identified from an initial screen of a million transformants. Of these, 24 were also b-galactosidase positives (gal+). Retransformation of these clones into a yeast strain expressing the LexA-PYK2-N fusion protein indicated that only one interacts with the PYK2 N-terminal domain (PYK2-N). The specificity of the interaction was further determined by transformation of this clone into a yeast strain expressing heterologous baits. An interaction was detected in yeast strain expressing either the PYK-N terminal domain, or a shorter version of PYK-N that was missing 48 amino acids from its C-terminal end. No interaction, however, was detected in strains expressing either the PYK-NN (amino acids 2–285), or the N-terminal domain of Fak, suggesting that this interaction is very specific.

The clone that scored for specific interaction with PYK2-N contained a partial cDNA which allowed subsequent isolation of a 3.1 kb cDNA with an open reading fram of 975 amino acids. The coding region was flanked by 5' and 3' untranslated regions of 93 and 149 bp respectively. The 5' untranslated region contains triplet repeats (CGG), a motif that was identified in many neuropsychiatric disorders. This region showed homology to the untranslated region of the human Fragile X mental retardation FMR-1 gene (66.3% match) using the Smith-Waterman algorithm.

A BLAST search with the full length cDNA sequence revealed that this protein is related to the drosophila retinal degeneration B protein (rdgB) and therefore it was named hrdgB1. The drosophila rdgB protein has an important role in phototransduction pathway. The rdgB mutant was initially identified by defects in the compound eye, in that rdgB mutant flies undergo light-enhanced photoreceptor cell degeneration. The drosophila rdgB protein contains a. phosphatidylinositol transfer domain (PI-TP) in its N-terminal portion, and a calcium binding site downstream. The protein contains six hydrophobic regions that were identified as transmembrane domains. The same hydrophobic regions are conserved in the hrdgB1 protein, however, analysis of rdgB1 sequence, as well as the drosophila homolog, using different algorithms (PROSITE) indicated that they are not classical transmembrane domains.

An ESTs data base search with drosophila rdgB sequence allowed the identification of two additional, human genes that belong to the same gene family. A PCR fragment derived from an EST fragment (T12574) was used as probe to screen a human brain cDNA library and subsequent isolation the hrdgB2 gene. The full length cDNA of hrdgB2 (4186 bp) contained an open reading of 1244 amino acids which was flanked by a 5' untranslated region of 174 bp and a 3' untranslated region of 280bp. The 257 amino-acids in the N-terminal end of the hrdgB2 protein have 41% similarity to the entire human PtdInsTP (M73704).

The full length cDNA of hrdgB3 was obtained by screening human brain and heart cDNA libraries. An initial clone of 1.8 kb was isolated from a human brain library using the PCR product derived from EST fragment (T12574) as a probe. A cDNA fragment derived from our 1.8 kb clone was used as a probe to screen a human heart cDNA library and allowed subsequent isolation of hrdgB3 gene. Two isoforms arising from alternative splicing have been identified by cDNA cloning, the longest which encodes a protein of 1349 amino-acids with a predicted molecular weight of 150 kDa, and a shorter one which lacks amino-acids 50–378, with a predicted molecular weight of 120 kDa. The coding sequence is flanked by a 79 bp 5' untranslated region and a 945 bp 3' untranslated region. The N-terminal region of hrdgB3 contains a PI-TP domain that is missing from the alternative spliced isoform. A strecht of glycines and serines was identified within amino acids 612–634 (78% glycine, 22% serine).

Multiple alignment analysis of the novel hrdgB1, hrdgB2 and hrdgB3 revealed high similarity in their primary structure: a PI-TP domain in the amino-terminal region, six conserved hydrophobic regions and very conserved C-terminal region. Unlike the other rdgB family members, hrdgB1 does not contain PtdInsTP domain, this may suggest that our clone represent an alternative spliced isoform.

EXAMPLE 2

Tissue Distribution of Human rdgBs

The levels of hrdgB1, hrdgB2 and hrdgB3 mRNA expression were determined by Northern analysis of various human tissues. HrdgB1 has a very restricted expression pattern. It is expressed in the brain, spleen and ovary as a message of approximately 7.5 kb. By contrast, hrdgB2 is highly expressed in many human tissues as a message of 4.5 kb. Highest levels of expression were detected in the brain, heart, thymus and peripheral blood leukocytes. HrdgB3 is very highly expressed in the thymus, but it is also expressed in the heart, brain, ovary and testis. Two messages were detected for hrdgB3: 7.5 kb and 9.5 kb messages that may represent the two alternative spliced isoforms that were isolated. The results discussed above indicate the rdgBs gene family members have very different expression patterns, whereas hrdgB1 is very rare, hrdgB2 is abundant and hrdgB3 has a unique pattern of expression.

EXAMPLE 3
Mapping the Minimal Interaction Domain of rdgB Proteins

To map the PYK2 interaction domain within the hrdgB1 protein, a series of hrdgB1-deletion mutants were constructed and their ability to interact with PYK2-N was tested utilizing the two hybrid system. Our original two hybrid clone containing amino acids 627–975 of hrdgB1 was used as a positive control. Deletion mutants were constructed, and among all these mutants, only hrdgB1-ΔIV, containing amino acids 627–936, interacts with PYK2-N terminal domain. The interaction of this domain with PYK2 was further confirmed by an in vitro binding experiment, showing binding of PYK2 to immobilized GST-fusion protein containing the same portion of hrdgB1. No binding was detected, however, to the GST-protein alone or between hrdgB1-ΔIV mutant and the focal adhesion kinase.

Since hrdgB1 shares high homology with hrdgB2 and hrdgB3 in their C-terminal domains, whether the corresponding regions of these two proteins interact with PYK2 was examined. For this purpose amino acids 911–1244 and 996–1350 of hrdgB2 and hrdgB3 respectively, were fused in frame to the activator domain of Gal-4, and their ability to interact with PYK2-N was tested by the two hybrid system. The results indicate that hrdgB2 can strongly bind to PYK2 N-terminal domain, whereas the interaction of rdgB3 with PYK2 is quite weak.

To further confirm this interaction in vivo, hrdgB2-HA or hrdgB3-HA were coexpressed either with PYK2 or with Fak in COS cells. Following cell lysis, hrdgB proteins were immunoprecipitated by anti-HA antibodies and the presence of PYK2 or Fak in the immunocomplexes was determined by immunoblotting with antibodies against PYK2 or Fak respectively. The results indicate that both hrdgB2 and hrsdgB3 interact with PYK2 in vivo. No interaction, however, was detected with the related kinase Fak, suggesting that hrdgBs proteins interact strongly and specifically with PYK2.

To explore whether the 'PYK2 binding domain' of hrdgBs is sufficient to confer association of those two proteins in vivo, a myc-tagged version of the hrdgB2 'PYK2-binding domain' was coexpressed either with PYK2 or with Fak in COS cells, and their interaction was analyzed. The results showed that this domain can interact with PYK2 in vivo and therefore represent a separate domain in this family of proteins.

EXAMPLE 4
In vivo Association of rdgB1 and PYK2

To confirm the interaction of hrdgB1 and PYK2 in vivo an hemagglutinin-tagged rdgB1 and PYK2 were coexpressed in 293 cells. The results indicate that hrdgB1 strongly associates with PYK2. Association of hrdgB1 with the related kinase Fak could not be detected under the same experimental conditions, suggesting a strong and specific interaction of hrdgB1 and PYK2.

To further characterize the interaction between hrdgB and PYK2, an adult rat brain was used as a source of these two proteins. When hrdgB1 was immunoprecipitated from a rat brain homogenate, utilizing specific antibodies against hrdgB1, PYK2 could be detected in the immunocomplex. However, the stochiometry of PYK2/rdgB1 interaction was not as high as shown in transfected cells. These results indicate that PYK2 and rdgB1 interact in vivo under physiological condition, and this interaction may have an important regulatory function in the brain.

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 3109 base pairs
      (B) TYPE: nucleic acid
      (C) STRANDEDNESS: single
      (D) TOPOLOGY: linear (xi) SEQUENCE DESCRIPTION: SEQ ID NO: 1:

```
GCGGCGGCGG CTGCGGTGGC GGCAGCGAGG CGAGCGGGGC GGGGGCGCGG GCGCGGCGCT      60

CGGAGTCCGT TCGGGGCCGG AGGCGGTCGG GGCCGGGCCC GGGAAGCGCG AGGAGCGCGC     120

GTAGCCGCCG GAGCCCGCCG CCCGGGACAT GGCCAAGGCG GGCCGTGCAG GTGGTCCTCC     180

CCCGGGCGGC GGTGCCCCCT GGCACCTTCG AAATGTCCTC AGTGACTCTG TGGAGAGCTC     240

AGATGATGAA TTCTTTGATG CCAGAGAGGA GATGGCTGAA GGGAAGAATG CCATCCTCAT     300

TGGGATGAGC CAGTGGAACT CCAATGACCT CGTGGAGCAG ATCGAGACCA TGGGGAAACT     360

GGACGAGCAT CAAGGAGAAG GGACCGCGCC GTGCACATCC AGCATCCTCC AGGAGAAGCA     420

GCGAGAACTG TACCGGGTTT CCTTGAGAAG ACAGAGGTTC CCAGCCCAGG GAAGCATCGA     480
```

```
GATCCACGAA GACAGCGAGG AAGGCTGCCC GCAGCGCTCC TGCAAGACAC ATGTCCTCCT    540

GCTGGTCCTG CATGGGGAA ACATCCTGGA CACGGGTGCC GGGGACCCGT CCTGCAAGGC    600

AGCCGACATC CACACCTTCA GCTCCGTGCT GGAGAAGGTC ACACGAGCCC ATTTCCCTGC    660

TGCCCTGGGC ACATCCTCA TCAAGTTCGT CCCCTGTCCT GCCATCTGCT CTGAGGCTTT    720

CTCGCTTGTC TCTCACCTGA ACCCCTACAG CCACGATGAG GGCTGCCTCA GCAGCAGCCA    780

GGACCACGTC CCTCTGGCCG CCCTTCCCCT GTTGGCCATC TCCTCCCCGC AGTACCAGGA    840

TGCTGTCGCC ACCGTCATCG AGCGAGCCAA CCAGGTCTAC AGAGAGTTCC TGAAGTCCTC    900

TGATGGGATT GGCTTCAGTG GCAGGTGTG TCTCATCGGG GACTGTGTGG GGGGCCTCCT    960

GGCCTTCGAT GCCATCTGCT ACAGTGCGGG GCCCTCAGGG GACAGCCCTG CCAGCAGCAG   1020

CCGGAAGGGG AGCATCAGCA GCACCCAGGA CACCCCAGTC GCGGTGGAGG AAGATTGCAG   1080

CCTGGCCAGC AGCAAGCGTC TCAGCAAAAG CAACATTGAC ATCTCCAGTG GGTTGGAGGA   1140

TGAGGAGCCC AAGAGGCCGT TGCCGCGGAA ACAGAGCGAC TCCTCCACCT ATGACTGCGA   1200

GGCCATCACC CAGCACCATG CCTTCCTCTC AAGCATCCAC TCCAGCGTGC TAAAGGATGA   1260

GTCTGAGACC CCGGCGGCTG GGGGGCCGCA GCTCCCTGAG GTCAGCCTGG GCCGCTTTGA   1320

CTTCGATGTG TCCGACTTCT TCCTCTTCGG CTCGCCACTG GGCCTGGTCC TGGCCATGCG   1380

GAGGACGGTG CTGCCTGGGC TGGACGGCTT CCAGGTGCGT CCTGCCTGCA GCCAGGTCTA   1440

CAGCTTCTTC CATTGCGCAG ACCCCTCTGC CTCACGGCTC GAGCCACTGC TGGAGCCCAA   1500

GTTCCACCTG GTGCCGCCTG TCAGCGTGCC TCGCTACCAG AGGTTCCCAC TGGGCGATGG   1560

GCAGTCCCTC CTCCTCGCTG ATGCCCTACA CACCCACAGC CCCTCTTCC TGGAGGGCAG   1620

CTCCCGGGAC AGCCCGCCAC TTCTGGATGC CCCTGCCTCG CCCCCTCAGG CCTCGAGGTT   1680

CCAGCGCCCA GGACGGAGGA TGAGCGAGGG GAGCTCCCAC AGCGAGAGCT CGGAGTCCTC   1740

GGACAGCATG GCACCCGTGG GTGCCTCCCG CATCACAGCC AAGTGGTGGG AAGCAAGAG   1800

GATCGACTAT GCCCTGTACT GCCCTGATGT CCTCACGGCC TTCCCCACCG TGGCCCTGCC   1860

CCACCTCTTC CACGCCAGTT ACTGGGAGTC CACAGACGTG GTGGCCTTCA TCCTGAGACA   1920

GGTAATGCGC TATGAGAGCG TGAACATCAA GGAAAGCGCC CGCCTGGACC CTGCAGCACT   1980

GAGTCCTGCC AACCCCCGGG AGAAGTGGCT TCGTAAGCGG ACTCAGGTCA AGCTGAGGAA   2040

TGTCACGGCT AATCACCGGG CCAATGATGT GATTGCTGCT GAAGATGGCC CCCAGGTCCT   2100

GGTGGGGCGG TTCATGTACG GGCCCCTCGA CATGGTGGCT CTGACTGGAG AGAAGGTGGA   2160

CATCCTAGTA ATGGCAGAGC CATCCTCAGG CCGCTGGGTA CACCTGGACA CAGAGATCAC   2220

CAACAGCAGT GGTCGCATCA CATACAATGT GCCGCGGCCC CGGCGCCTGG GGGTTGGTGT   2280

CTATCCTGTG AAGATGGTCG TCAGGGCGA CCAGACCTGT GCCATGAGCT ACCTCACGGT   2340

GTTGCCCAGG GGCATGGAGT GTGTAGTGTT CAGCATTGAT GGGTCCTTCG CGGCCAGCGT   2400

GTCTATCATG GGAAGCGACC CCAAGGTCCG GCCGGGTGCA GTGGATGTTG TCCGGCACTG   2460

GCAGGACTTG GGCTACATGA TCCTTTACAT CACGGGACGG CCGGACATGC AGAAGCAGCG   2520

GGTGGTGTCG TGGCTGTCCC AGCACAACTT CCCACAGGGC ATGATCTTCT TCTCCGACGG   2580

GCTGGTGCAT GACCCGCTGC GGCAGAAGGC CATCTTCCTG CGCAACCTCA TGCAGGAGTG   2640

CTTCATCAAA ATCAGTGCGG CCTATGGCTC CACGAAGGAC ATCTCTGTCT ACAGCGTGCT   2700

GGGCCTGCCT GCCTCCCAGA TCTTCATTGT GGGCCGGCCC ACCAAGAAGT ACCAAACCCA   2760

GTGCCAGTTC CTGAGCGAGG GCTACGCCGC ACACCTGGCC GTGCTGGAGG CCAGCCACCG   2820
```

| | | | | |
|---|---|---|---|---|
|CTCACGCCCA | AAGAAGAACA | ACTCGCGCAT | GATCCTGCGC | AAGGGCAGCT TCGGGCTGCA | 2880|
|CGCGCAGCCA | GAGTTCCTGC | GGAAGCGCAA | CCACCTGCGC | AGAACCATGT CAGTGCAGCA | 2940|
|GCCCGACCCG | CCCGCCGCCA | ACCCCAAGCC | CGAGCGGGCC | CAGAGCCAGC CCGAGTCGGA | 3000|
|CAAAGACCAC | GAGCGGCCGC | TGCCGGCGCT | CAGCTGGGCG | CGTGGGCCCC CCAAGTTCGA | 3060|
|GTCGGTGCCC | TGAGGGGTGG | GCTGTGCTCA | GAGCAGGGAG | CGGGGGCCG | 3109|

(2) INFORMATION FOR SEQ ID NO: 2:

(i) SEQUENCE CHARACTERISTICS:
        (A) LENGTH: 4190 base pairs
        (B) TYPE: nucleic acid
        (C) STRANDEDNESS: single
        (D) TOPOLOGY: linear (xi) SEQUENCE DESCRIPTION: SEQ ID NO: 2:

| | | | | |
|---|---|---|---|---|
|CCGGCACTGC | GCCTCGGGAG | GGTCCGGCCA | CCGCTGGAAC | CCGAGGCCGG GGCTGGGGGC | 60|
|GCTCCGGGCT | CCGACCCACG | GGCCGGCCGG | CCCTGCCCGG | GCTGGGTGAG GGGCGCCCGC | 120|
|CTCAAGCTAG | AGGAGGAGCG | GAGGCCGCGC | GCGGCCCGCC | GAGCGCCTTC AGGATGCTCA | 180|
|TCAAGGAATA | CCACATTCTG | CTGCCCATGA | GCCTGGACGA | GTACCAGGTG GCCCAGCTCT | 240|
|ACATGATCCA | GAAAAAGAGC | CGGGAGGAGT | CTAGTGGTGA | GGGCAGCGGC GTGGAGATCC | 300|
|TGGCCAACCG | GCCCTACACG | GATGGGCCCG | GGGCAGCGG | GCAATACACA CACAAGGTGT | 360|
|ACCACGTGGG | CTCCCACATC | CCAGGCTGGT | TCCGGGCACT | GCTGCCCAAG CTGCCCTGC | 420|
|AGGTAGAAGA | GGAATCCTGG | AATGCCTACC | CCTACACCCG | AACCCGGTAC ACCTGCCCTT | 480|
|TCGTGGAGAA | ATTCTCCATT | GAAATTGAGA | CCTATTACCT | GCCTGATGGG GGGCAGCAGC | 540|
|CAAACGTCTT | CAACCTGAGC | GGGGCCGAGA | GGAGACAGCG | CATCCTGGAC ACCATCGACA | 600|
|TCGTGCGGGA | TGCAGTGGCC | CCAGGCGAGT | ACAAAGCAGA | AGAGGACCCC CGGCTTTATC | 660|
|ACTCGGTCAA | GACGGGCCGA | GGGCCACTGT | CTGATGACTG | GCACGGACG GCGGCACAGA | 720|
|CGGGGCCCCT | TATGTGTGCC | TATAAGCTGT | GCAAGGTTGA | GTTCCGCTAC TGGGGCATGC | 780|
|AAGCCAAGAT | CGAGCAGTTC | ATCCATGATG | TAGGTCTGCG | TCGGGTGATG CTGCGGGCCC | 840|
|ACCGCCAGGC | CTGGTGCTGG | CAGGATGAGT | GGACAGAGCT | GAGCATGGCT GACATCCGGG | 900|
|CACTGGAAGA | GGAGACTGCT | CGCATGCTGG | CCCAGCGCAT | GGCCAAGTGC AACACAGGCA | 960|
|GTGAGGGGTC | CGAGGCCCAG | CCCCCCGGGA | AACCGAGCAC | CGAGGCCCGG TCTGCGGCCA | 1020|
|GCAACACTGG | CACCCCCGAT | GGGCCTGAGG | CCCCCCCAGG | CCCAGATGCC TCCCCCGATG | 1080|
|CCAGCTTTGG | GAAGCAGTGG | TCCTCATCCT | CCCGTTCCTC | CTACTCATCC AACATGGAG | 1140|
|GGGCTGTGTC | TCCCCAGAGC | TTGTCTGAGT | GGCGCATGCA | GAACATTGCC CGAGACTCTG | 1200|
|AGAACAGCTC | CGAGGAAGAG | TTCTTTGATG | CCCACGAAGG | CTTCTCGGAC AGTGAGGAGG | 1260|
|TCTTCCCCAA | GGAGATGACC | AAGTGGAACT | CCAATGACTT | CATTGATGCC TTTGCCTCCC | 1320|
|CAGTGGAGGC | AGAGGGAACG | CCAGAGCCTG | GAGCCGAGGC | AGCTAAAGGC ATTGAGGATG | 1380|
|GGCCCAAGC | ACCCAGGGAC | TCAGAGGGCC | TGGATGGAGC | CGGGGAGCTG GGGGCTGAGG | 1440|
|CATGCGCAGT | CCACGCCCTC | TTCCTTATCC | TGCACAGCGG | CAACATCCTG GACTCAGGCC | 1500|
|CTGGAGACGC | CAACTCCAAG | CAGGCGGATG | TGCAGACGCT | GAGCTCCGCC TTCGAGGCCG | 1560|
|TCACCCGCAT | CCACTTCCCT | GAGGCCTTGG | GCCACGTGGC | GCTGCGACTG GTGCCCTGTC | 1620|
|CACCCATCTG | CGCCGCCGCC | TATGCCCTTG | TCTCCAACCT | GAGCCCTTAC AGCCACGATG | 1680|
|GGGACAGCCT | GTCTCGCTCC | CAAGACCACA | TTCCACTGGC | TGCCCTGCCA CTGCTGGCCA | 1740|

-continued

```
CCTCATCCTC CCGCTACCAG GGCGCCGTGG CCACCGTCAT TGCCCGCACC AACCAGGCCT    1800

ACTCAGCCTT CCTGCGCTCA CCTGAGGGTG CCGGCTTCTG TGGGCAGGTC GCACTGATTG    1860

GAGATGGTGT TGGTGGCATC CTGGGCTTTG ATGCACTCTG CCACAGTGCT AACGCGGGCA    1920

CCGGGAGTCG GGGCAGCAGC CGCCGTGGGA GCATGAACAA TGAGCTGCTC TCTCCGGAGT    1980

TTGGCCCAGT GCGGGACCCC CTGGCAGATG GTGTGGAAGG CCTGGGTCGG GGCAGCCCAG    2040

AACCCTCGGC CTTGCCTCCC CAGCGCATCC CCAGCGACAT GGCCAGTCCT GAGCCCGAGG    2100

GCTCTCAGAA CAGCCTTCAG GCAGCCCCG  CAACCACCTC CTCCTGGGAG CCCCGGCGGG    2160

CAAGCACGGC CTTCTGCCCA CCCGCTGCCA GTTCCGAGGC ACCTGACGGC CCCAGCAGCA    2220

CTGCCCGCCT TGACTTCAAG GTCTCTGGCT TCTTCCTCTT CGGCTCCCCA CTGGGCCTGG    2280

TGCTGGCTCT GCGCAAAACT GTGATGCCCG CCCTGGAGGC AGCCCAGATG CGCCCAGCCT    2340

GTGAACAGAT CTACAACCTC TTCCACGCGG CCGACCCCTG CGCCTCACGC CTCGAGCCCC    2400

TGCTGGCCCC GAAGTTCCAG GCCATCGCCC CACTGACCGT GCCCCGCTAC CAGAAGTTCC    2460

CCCTGGGAGA TGGCTCATCC CTGCTGCTGG CCGACACTCT GCAGACGCAC TCCAGCCTCT    2520

TTCTGGAGGA GCTGGAGATG CTGGTGCCCT CAACACCCAC CTCTACTAGC GGTGCCTTCT    2580

GGAAGGGCAG TGAGTTGGCC ACTGACCCCC CGGCCCAGCC AGCCGCCCCC AGCACCACCA    2640

GTGAGGTGGT TAAGATCCTG GAGCGCTGGT GGGGGACCAA GCGGATCGAC TACTCGCTGT    2700

ACTGCCCCGA GGCGCTCACC GCCTTTCCCA CCGTCACGCT GCCCCACCTC TTCCACGCCA    2760

GCTACTGGGA GTCCGCCGAC GTGGTGGCGT TCATCCTGCG CCAGGTGATC GAGAAGGAGC    2820

GGCCACAGCT GGCGGAATGC GAGGAGCCGT CCATCTACAG CCCGGCCTTC CCCAGGGAGA    2880

AGTGGCAGCG AAAACGCACG CAGGTCAAGA TCCGGAACGT CACTTCCAAC CACCGGGCGA    2940

GCGACACGGT GGTGTGCGAG GGGCCGCCCC AGGTGCTAAG CGGGCGCTTC ATGTACGGGC    3000

CCCTGGACGT CGTCACGCTC ACTGGAGAGA AGGTGGATGT CTACATCATG ACGCAGCCGC    3060

TGTCGGGCAA GTGGATCCAC TTTGGCACCG AAGTCACCAA TAGCTCGGGC CGCCTCACCT    3120

TCCCAGTTCC CCCAGAACGC GCGCTGGGCA TTGGTGTCTA CCCCGTGCGC ATGGTGGTCA    3180

GGGGCGACCA CACCTATGCC GAATGCTGCC TGACTGTGGT GGCCCGCGGC ACGGAGGCTG    3240

TGGTCTTCAG CATCGACGGC TCCTTCACCG CCAGCGTCTC CATCATGGGC AGCGACCCCA    3300

AGGTGCGAGC TGGCGCCGTG GACGTGGTCA GGCACTGGCA GGACTCCGGC TACCTGATCG    3360

TGTATGTCAC AGGCCGGCCG GATATGCAGA AGCACCGCGT GGTGGCATGG CTGTCGCAGC    3420

ACAACTTCCC CCACGGCGTC GTCTCCTTCT GCGACGGCCT CACCCACGAC CCACTACGCC    3480

AGAAGGCAAT GTTTCTGCAG AGCCTGGTGC AGGAGGTAGA ACTGAACATC GTGGCCGGTT    3540

ATGGGTCTCC CAAAGATGTG GCTGTATACG CGGCGCTGGG GCTGTCCCCG AGCCAGACCT    3600

ACATCGTGGG CCGTGCCGTG CGGAAGCTAC AGGCGCAGTG CCAGTTCCTG TCAGACGGCT    3660

ATGTGGCCCA CCTGGGCCAG CTGGAAGCGG GCTCGCACTC GCATGCCTCC TCGGGACCCC    3720

CGAGAGCTGC CTTGGGCAAG AGCAGCTATG GTGTGGCTGC CCCCGTGGAC TTCCTGCGCA    3780

AACAGAGCCA GCTGCTTCGC TCGAGGGGCC CCAGCCAGGC GGAGCGTGAG GGCCCGGGAA    3840

CACCACCCAC CACCCTGGCA CGGGGCAAAG CACGGAGCAT CAGCCTGAAG CTGGACAGCG    3900

AGGAGTGAGG CCCACACCAG CCTGGACCTG GGTTATTTAT TGACACACCC AAGGGGCCCG    3960

AGGGGCTGCG TGTGGGGAGG CTGGGGACCC AGACTTTTGG CCCCAGCGCT GGCCCCCCCA    4020

GCCCCACACC CTATATCTCC GTGTGCTCCT CGGTGTTACT TCCCTTTCAT ATGAGGGGAC    4080

CCAGCGCCGG GGGGAGGGAG GAGGGCGTGG GCATGGGCGC AGAGGCTTTT CCAGTGTGTA    4140
```

```
TAAATCCATG AAAATAAACG CCACCTGCAC CCTAAAAAAA AAAAGTCGAC        4190
```

(2) INFORMATION FOR SEQ ID NO: 3:

(i) SEQUENCE CHARACTERISTICS:
        (A) LENGTH: 5020 base pairs
        (B) TYPE: nucleic acid
        (C) STRANDEDNESS: single
        (D) TOPOLOGY: linear (xi) SEQUENCE DESCRIPTION: SEQ ID NO: 3:

```
GCGGCCGCGT CGACAAGGAA CCTTGCCTAG AAGTCCCAAC TTGCAGTTCC CCATCGACGG          60
GAAGGCTTGG ACTCCAAGAT GATTATAAAG GAATATCGGA TTCCTCTGCC AATGACCGTG         120
GAGGAGTACC GCATCGCCCA GCTGTACATG ATACAGAAGA GAGCCGTAA CGAGACATAT         180
GGCGAAGGCA GCGGCGTGGA GATCCTGGAG AACCGGCCGT ACACAGATGG CCCAGGCGGC         240
TCTGGGCAGT ACACACACAA GGTGTATCAT GTGGGCATGC ACATTCCCAG CTGGTTCCGC         300
TCCATCCTGC CCAAGGCAGC CCTGCGGGTG GTGGAGGAGT CTTGGAATGC CTACCCCTAC         360
ACCCGAACCA GGTTCACCTG TCCTTTCGTG GAGAAATTCT CCATCGACAT TGAAACCTTT         420
TATAAAACTG ATGCTGGAGA AAACCCCGAC GTGTTCAACC TCTCTCCTGT GGAAAAGAAC         480
CAGCTGACAA TCGACTTCAT CGACATTGTC AAAGACCCTG TGCCCCACAA CGAGTATAAG         540
ACAGAAGAGG ACCCCAAGCT GTTCCAGTCA ACCAAGACCC AGCGGGGGCC CCTGTCCGAG         600
AACTGGATCG AGGAGTACAA GAAGCAGGTC TTCCCCATCA TGTGCGCATA CAAGCTCTGC         660
AAGGTGGAGT TCCGCTACTG GGGCATGCAG TCCAAGATCG AGAGGTTCAT CCACGACACC         720
GGACTACGGA GGGTGATGGT GCGGGCTCAC CGGCAGGCCT GGTGCTGGCA GGACGAGTGG         780
TATGGGCTGA GCATGGAGAA CATCCGGGAG CTGGAGAAGG AGGCACAGCT CATGCTTTCC         840
CGTAAGATGG CCCAGTTCAA TGAGGATGGT GAGGAGGCCA CTGAGCTCGT CAAGCACGAA         900
GCCGTCTCGG ACCAGACCTC TGGGGAGCCC CCGGAGCCCA GCAGCAGCAA TGGGGAGCCC         960
CTAGTGGGGC GCGGCCTCAA GAAACAGTGG TCCACATCCT CCAAGTCGTC TCGGTCGTCC        1020
AAGCGGGGAG CGAGTCCTTC CCGCCACAGC ATCTCAGAGT GGAGGATGCA GAGTATTGCC        1080
AGGGACTCGG ATGAGAGCTC AGATGATGAG TTCTTCGATG CGCACGAGGA CCTGTCCGAC        1140
ACAGAGGAAA TGTTCCCCAA GGACATCACC AAGTGGAGCT CCAATGACCT CATGGACAAG        1200
ATCGAGAGCC CAGAGCCGGA AGACACACAA GATGGTCTGT ACCGCCAGGG TGCCCCTGAG        1260
TTCAGGGTGG CCTCCAGTGT GGAGCAGCTG AACATCATAG GGACGAGGT TAGCCAGCCG        1320
CTGGCTGCAC CGCCCTCCAA GATCCACGTG CTGCTATTGG TGCTGCACGG AGGCACCATC        1380
CTGGACACAG GCGCCGGGA CCCCAGCTCC AAGAAGGGCG ATGCTAACAC CATCGCCAAC        1440
GTGTTCGACA CCGTCATGCG CGTGCACTAC CCCAGCGCCC TGGGCCGCCT TGCCATCCGC        1500
CTGGTGCCCT GCCCGCCCGT CTGCTCTGAC GCCTTTGCCC TGGTCTCCAA CCTCAGCCCC        1560
TACAGCCATG ACGAAGGCTG TCTGTCCAGC AGTCAGGACC ACATTCCCCT GGCTGCCCTC        1620
CCCCTGCTGG CCACCTCCTC CCCCCAGTAC CAGGAGGCAG TTGCCACAGT GATTCAGCGA        1680
GCCAACCTTG CCTATGGGGA CTTCATCAAG TCCCAGGAGG GCATGACCTT CAATGGGCAG        1740
GTCTGCCTGA TTGGGACTG CGTCGGGGGC ATCCTGGCAT TTGATGCCCT GTGCTACAGT        1800
AACCAGCCGG TGTCTGAGAG TCAGAGCAGC AGCCGCCGGG GCAGCGTGGT CAGCATGCAG        1860
GACAATGACC TGCTGTCCCC GGGCATCCTG ATGAATGCAG CACACTGCTG CGGTGGTGGC        1920
GGTGGCGGCG GTGGCGGTGG TGGCAGCAGT GGTGGTGGTG GCAGTAGTGG TGGCTCCAGC        1980
```

```
CTGGAGAGCA GTCGGCACCT GAGCCGAAGC AACGTCGACA TCCCCCGCAG CAACGGCACT   2040

GAGGACCCCA AAAGGCAACT GCCCCGCAAG AGGAGCGACT CATCCACCTA CGAGCTGGAT   2100

ACCATCCAGC AGCACCAGGC CTTCCTGTCC AGCCTCCATG CCAGCGTGCT GAGGACTGAG   2160

CCCTGCTCAC GCCATTCCAG CAGCTCCACC ATGCTGGATG GCACAGGTGC CCTGGGCAGG   2220

TTTGACTTTG AGATCACCGA CCTCTTCCTC TTCGGGTGCC CGCTGGGGCT GGTCCTGGCC   2280

TTGAGGAAGA CTGTCATCCC AGCCCTGGAT GTTTTCCAGC TGCGGCCGGC CTGCCAGCAA   2340

GTCTACAACC TCTTCCACCC CGCGGACCCG TCAGCTTCAC GCCTGGAGCC GCTGCTGGAA   2400

CGGCGCTTTC ACGCCCTGCC GCCTTTCAGC GTCCCCCGCT ACCAACGCTA CCCGCTGGGG   2460

GATGGCTGCT CCACGCTGCT GGCGGATGTG CTCCAGACCC ACAATGCAGC CTTCCAAGAG   2520

CATGGCGCCC CCTCCTCGCC GGGCACTGCC CCTGCCAGTC GTGGCTTCCG CCGAGCCAGT   2580

GAGATCAGCA TCGCCAGCCA GGTGTCAGGC ATGGCTGAGA GCTACACGGC ATCCAGCATC   2640

GCCCAGAAGG CCCCCGATGC GCTCAGCCAT ACCCCAGCG TCAGGCGTCT GTCCCTGCTC   2700

GCCCTGCCCG CCCCCAGCCC CACCACCCCT GGCCCCCACC CTCCAGCCAG GAAGGCAAGC   2760

CCTGGCCTGG AGAGGGCCCC TGGCCTCCCT GAGCTGGACA TTGGAGAAGT CGCTGCAAAG   2820

TGGTGGGGCC AGAAGCGGAT CGACTACGCC CTGTACTGCC CTGACGCCCT CACGGCCTTC   2880

CCCACGGTGG CTCTGCCTCA CCTCTTCCAC GCCAGCTACT GGGAGTCAAC AGACGTGGTC   2940

TCCTTTCTGC TGAGACAGGT CATGAGGCAT GACAACTCCA GCATCTTGGA GCTGGATGGC   3000

AAGGAAGTGT CGGTGTTCAC CCCCTCAAAG CCAAGGGAGA AGTGGCAGCG CAAGCGGACC   3060

CACGTGAAGC TGCGGAACGT GACGGCCAAC CACCGGATCA ATGATGCCCT TGCCAATGAG   3120

GACGGCCCCC AGGTTCTGAC GGGCAGGTTC ATGTATGGGC CCCTGGACAT GGTCACCCTG   3180

ACTGGGGAGA AGGTGGATGT GCACATCATG ACCCAGCCGC CCTCAGGCGA GTGGCTCTAC   3240

CTGGATACGC TGGTGACCAA CAACAGTGGG CGTGTCTCCT ACACCATCCC TGAGTCGCAC   3300

CGCCTGGGCG TGGGTGTCTA CCCTATCAAG ATGGTGGTCA GGGGAGACCA CACGTTTGCC   3360

GACAGCTACA TCACCGTGCT GCCCAAGGGC ACAGAGTTCG TGGTCTTCAG CATCGACGGT   3420

TCCTTTGCCG CTAGCGTGTC CATCATGGGC AGCGACCCCA AGGTGCGGGC CGGGGCCGTG   3480

GACGTGGTGC GGCACTGGCA GGACCTGGGC TACCTCATCA TCTACGTGAC GGGCCGGCCC   3540

GACATGCAGA AGCAGCGGGT GGTGGCGTGG CTGGCCCAGC ACAACTTCCC CCATGGCGTG   3600

GTGTCCTTCT GTGACGGCCT GGTGCATGAC CCGCTGCGGC ACAAGGCCAA CTTCCTGAAG   3660

CTGCTCATCT CCGAGCTGCA CCTGCGCGTG CACGCGGCCT ATGGCTCCAC CAAGGACGTG   3720

GCGGTGTACA GCGCCATTAG CCTGTCCCCC ATGCAGATCT ACATCGTGGG CCGGCCCACC   3780

AAGAAGCTGC AGCAGCAGTG CCAGTTCATC ACGGATGGCT ACGCGGCCCA CCTGGCGCAG   3840

CTGAAGTACA GCCACCGGGC GCGGCCCGCT CGCAACACGG CCACCCGCAT GGCGCTGCGC   3900

AAGGGCAGCT TCGGCCTGCC CGGCCAGGGC GACTTTCTGC GCTCCCGGAA CCACCTGCTT   3960

CGCACCATCT CGGCCCAGCC CAGCGGGCCC AGCACCGGCC ACGAGCGGAC ACAGAGCCAG   4020

GCGGATGGCG AGCAGCGGGG CCAGCGCAGC ATGAGTGTGG CGGCCGGCTG CTGGGCCGC   4080

GCCATGACTG GCCGCCTGGA GCCGGGGGCA GCCGCGGGCC CCAAGTAGGG CACCGTGAGT   4140

GCAGCGCGGG GTCTCCATGG TGCTAGGCCA GGGTGGCCAG CCCCGCCAGG AGGCCTGGCC   4200

TGGGCACACG CACTGACGTG GGCCTGGGAG ATTGTCCCAG GGCCTTGTGG AGGACACGGG   4260

CCGCACCACA CAGTGCTCCC TGCCCTGCCT CACGTCCTCG GGCCTGACGG GTCCGGCTTG   4320
```

-continued

```
TCATGGAAGC TGGCAGGGAC CACCAGCCCC AGGATGGCAG AGGGACCAGA ACCTCCCACT    4380

CAGACTGGCC CGGGAGGTTC TCCCAGACAT TTTGCCCTGT GTGGATCTCC AAGTGTCCTG    4440

GTGCCAGGTG TGGGCCCAGG CGCAGCCTGC CACCTCCCCA TCCACTGGCC ACCCTCACTC    4500

CCAGGTCCCC TCCCATTTGG TAGCAGCTCC AACAGGGGTC CAGCCTGCAT CTTGTTAACT    4560

CGAGTTTCTC AACTGTTCAA CCTCACTGGT TTTGCACTGA TTTTTGAGAG CGGAGACCCA    4620

TTACCACCTC CTATGGCTAC AGCCCCGTTG ACATGCATGA AACTCAGTAC CTGCTGACCC    4680

AGGACCTACA ACCACACTGA AGGCTCCAGT GCGGCAGAGC CTCGTGCAAG CAGGAGAGAA    4740

AGGCTGTATC TTAATTTCTG CACCCCGGAC CCTGCCCACC TGTCTGCCTG CCCCGCCTGG    4800

AGCCCAGGCC AGTGTTGTTT CCAGCCTCAG GCCACGGGCT GGACGGGCCT GGCCGCCTCT    4860

TCCGCTCCCT GCCATCAGTC AAGGCCGCCC GCCCACGTTT CTACGCCTTT CTACTTCTCA    4920

ATCTGATTTC TATGAGGTTT TTTTAAACGA GCAATCCTTG GCTGCTTCCT TTTCTTAACT    4980

CTTTCAGTAC TGAGAGCAGC CCCTCCGTCG ACGCGGCCGC                         5020
```

(2) INFORMATION FOR SEQ ID NO: 4:

(i) SEQUENCE CHARACTERISTICS:
        (A) LENGTH: 974 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Met Ala Lys Ala Gly Arg Ala Gly Gly Pro Pro Gly Gly Gly Ala
 1               5                  10                  15

Pro Trp His Leu Arg Asn Val Leu Ser Asp Ser Val Glu Ser Asp
                20                  25                  30

Asp Glu Phe Phe Asp Ala Arg Glu Met Ala Glu Gly Lys Asn Ala
                35                  40                  45

Ile Leu Ile Gly Met Ser Gln Trp Asn Ser Asn Asp Leu Val Glu Gln
50                  55                  60

Ile Glu Thr Met Gly Lys Leu Asp Glu His Gln Gly Glu Gly Thr Ala
65                  70                  75                  80

Pro Cys Thr Ser Ser Ile Leu Gln Glu Lys Gln Arg Glu Leu Tyr Arg
                85                  90                  95

Val Ser Leu Arg Arg Gln Arg Phe Pro Ala Gln Gly Ser Ile Glu Ile
                100                 105                 110

His Glu Asp Ser Glu Glu Gly Cys Pro Gln Arg Ser Cys Lys Thr His
                115                 120                 125

Val Leu Leu Val Leu His Gly Gly Asn Ile Leu Asp Thr Gly Ala
                130                 135                 140

Gly Asp Pro Ser Cys Lys Ala Ala Asp Ile His Thr Phe Ser Ser Val
145                 150                 155                 160

Leu Glu Lys Val Thr Arg Ala His Phe Pro Ala Ala Leu Gly His Ile
                165                 170                 175

Leu Ile Lys Phe Val Pro Cys Pro Ala Ile Cys Ser Glu Ala Phe Ser
                180                 185                 190

Leu Val Ser His Leu Asn Pro Tyr Ser His Asp Glu Gly Cys Leu Ser
                195                 200                 205

Ser Ser Gln Asp His Val Pro Leu Ala Ala Leu Pro Leu Leu Ala Ile
                210                 215                 220
```

-continued

```
Ser Ser Pro Gln Tyr Gln Asp Ala Val Ala Thr Val Ile Glu Arg Ala
225                 230                 235                 240

Asn Gln Val Tyr Arg Glu Phe Leu Lys Ser Ser Asp Gly Ile Gly Phe
            245                 250                 255

Ser Gly Gln Val Cys Leu Ile Gly Asp Cys Val Gly Gly Leu Leu Ala
        260                 265                 270

Phe Asp Ala Ile Cys Tyr Ser Ala Gly Pro Ser Gly Asp Ser Pro Ala
    275                 280                 285

Ser Ser Ser Arg Lys Gly Ser Ile Ser Ser Thr Gln Asp Thr Pro Val
290                 295                 300

Ala Val Glu Glu Asp Cys Ser Leu Ala Ser Ser Lys Arg Leu Ser Lys
305                 310                 315                 320

Ser Asn Ile Asp Ile Ser Ser Gly Leu Glu Asp Glu Pro Lys Arg
            325                 330                 335

Pro Leu Pro Arg Lys Gln Ser Asp Ser Ser Thr Tyr Asp Cys Glu Ala
            340                 345                 350

Ile Thr Gln His His Ala Phe Leu Ser Ser Ile His Ser Ser Val Leu
            355                 360                 365

Lys Asp Glu Ser Glu Thr Pro Ala Ala Gly Gly Pro Gln Leu Pro Glu
370                 375                 380

Val Ser Leu Gly Arg Phe Asp Phe Asp Val Ser Asp Phe Phe Leu Phe
385                 390                 395                 400

Gly Ser Pro Leu Gly Leu Val Leu Ala Met Arg Arg Thr Val Leu Pro
            405                 410                 415

Gly Leu Asp Gly Phe Gln Val Arg Pro Ala Cys Ser Gln Val Tyr Ser
            420                 425                 430

Phe Phe His Cys Ala Asp Pro Ser Ala Ser Arg Leu Glu Pro Leu Leu
            435                 440                 445

Glu Pro Lys Phe His Leu Val Pro Pro Val Ser Val Pro Arg Tyr Gln
            450                 455                 460

Arg Phe Pro Leu Gly Asp Gly Gln Ser Leu Leu Ala Asp Ala Leu
465                 470                 475                 480

His Thr His Ser Pro Leu Phe Leu Glu Gly Ser Ser Arg Asp Ser Pro
            485                 490                 495

Pro Leu Leu Asp Ala Pro Ala Ser Pro Pro Gln Ala Ser Arg Phe Gln
            500                 505                 510

Arg Pro Gly Arg Arg Met Ser Glu Gly Ser Ser His Ser Glu Ser Ser
            515                 520                 525

Glu Ser Ser Asp Ser Met Ala Pro Val Gly Ala Ser Arg Ile Thr Ala
            530                 535                 540

Lys Trp Trp Gly Ser Lys Arg Ile Asp Tyr Ala Leu Tyr Cys Pro Asp
545                 550                 555                 560

Val Leu Thr Ala Phe Pro Thr Val Ala Leu Pro His Leu Phe His Ala
            565                 570                 575

Ser Tyr Trp Glu Ser Thr Asp Val Val Ala Phe Ile Leu Arg Gln Val
            580                 585                 590

Met Arg Tyr Glu Ser Val Asn Ile Lys Glu Ser Ala Arg Leu Asp Pro
            595                 600                 605

Ala Ala Leu Ser Pro Ala Asn Pro Arg Glu Lys Trp Leu Arg Lys Arg
            610                 615                 620

Thr Gln Val Lys Leu Arg Asn Val Thr Ala Asn His Arg Ala Asn Asp
625                 630                 635                 640

Val Ile Ala Ala Glu Asp Gly Pro Gln Val Leu Val Gly Arg Phe Met
```

```
                    645                 650                 655
Tyr Gly Pro Leu Asp Met Val Ala Leu Thr Gly Glu Lys Val Asp Ile
            660                 665                 670
Leu Val Met Ala Glu Pro Ser Ser Gly Arg Trp Val His Leu Asp Thr
            675                 680                 685
Glu Ile Thr Asn Ser Ser Gly Arg Ile Thr Tyr Asn Val Pro Arg Pro
            690                 695                 700
Arg Arg Leu Gly Val Gly Val Tyr Pro Val Lys Met Val Val Arg Gly
705                 710                 715                 720
Asp Gln Thr Cys Ala Met Ser Tyr Leu Thr Val Leu Pro Arg Gly Met
            725                 730                 735
Glu Cys Val Val Phe Ser Ile Asp Gly Ser Phe Ala Ala Ser Val Ser
            740                 745                 750
Ile Met Gly Ser Asp Pro Lys Val Arg Pro Gly Ala Val Asp Val Val
            755                 760                 765
Arg His Trp Gln Asp Leu Gly Tyr Met Ile Leu Tyr Ile Thr Gly Arg
            770                 775                 780
Pro Asp Met Gln Lys Gln Arg Val Val Ser Trp Leu Ser Gln His Asn
785                 790                 795                 800
Phe Pro Gln Gly Met Ile Phe Phe Ser Asp Gly Leu Val His Asp Pro
            805                 810                 815
Leu Arg Gln Lys Ala Ile Phe Leu Arg Asn Leu Met Gln Glu Cys Phe
            820                 825                 830
Ile Lys Ile Ser Ala Ala Tyr Gly Ser Thr Lys Asp Ile Ser Val Tyr
            835                 840                 845
Ser Val Leu Gly Leu Pro Ala Ser Gln Ile Phe Ile Val Gly Arg Pro
850                 855                 860
Thr Lys Lys Tyr Gln Thr Gln Cys Gln Phe Leu Ser Glu Gly Tyr Ala
865                 870                 875                 880
Ala His Leu Ala Val Leu Glu Ala Ser His Arg Ser Arg Pro Lys Lys
            885                 890                 895
Asn Asn Ser Arg Met Ile Leu Arg Lys Gly Ser Phe Gly Leu His Ala
            900                 905                 910
Gln Pro Glu Phe Leu Arg Lys Arg Asn His Leu Arg Arg Thr Met Ser
            915                 920                 925
Val Gln Gln Pro Asp Pro Ala Ala Asn Pro Lys Pro Glu Arg Ala
930                 935                 940
Gln Ser Gln Pro Glu Ser Asp Lys Asp His Glu Arg Pro Leu Pro Ala
945                 950                 955                 960
Leu Ser Trp Ala Arg Gly Pro Pro Lys Phe Glu Ser Val Pro
            965                 970
```

(2) INFORMATION FOR SEQ ID NO: 5:

(i) SEQUENCE CHARACTERISTICS:
        (A) LENGTH: 1244 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Met Leu Ile Lys Glu Tyr His Ile Leu Pro Met Ser Leu Asp Glu
1               5                   10                  15
Tyr Gln Val Ala Gln Leu Tyr Met Ile Gln Lys Lys Ser Arg Glu Glu
```

```
                    20                  25                  30
Ser Ser Gly Glu Gly Ser Gly Val Glu Ile Leu Ala Asn Arg Pro Tyr
            35                  40                  45
Thr Asp Gly Pro Gly Gly Ser Gly Gln Tyr Thr His Lys Val Tyr His
        50                  55                  60
Val Gly Ser His Ile Pro Gly Trp Phe Arg Ala Leu Leu Pro Lys Ala
65                  70                  75                  80
Ala Leu Gln Val Glu Glu Ser Trp Asn Ala Tyr Pro Tyr Thr Arg
                85                  90                  95
Thr Arg Tyr Thr Cys Pro Phe Val Lys Phe Ser Ile Glu Ile Glu
                100                 105                 110
Thr Tyr Tyr Leu Pro Asp Gly Gln Gln Pro Asn Val Phe Asn Leu
            115                 120                 125
Ser Gly Ala Glu Arg Arg Gln Arg Ile Leu Asp Thr Ile Asp Ile Val
        130                 135                 140
Arg Asp Ala Val Ala Pro Gly Glu Tyr Lys Ala Glu Asp Pro Arg
145                 150                 155                 160
Leu Tyr His Ser Val Lys Thr Gly Arg Gly Pro Leu Ser Asp Asp Trp
                165                 170                 175
Ala Arg Thr Ala Ala Gln Thr Gly Pro Leu Met Cys Ala Tyr Lys Leu
            180                 185                 190
Cys Lys Val Glu Phe Arg Tyr Trp Gly Met Gln Ala Lys Ile Glu Gln
            195                 200                 205
Phe Ile His Asp Val Gly Leu Arg Arg Val Met Leu Arg Ala His Arg
210                 215                 220
Gln Ala Trp Cys Trp Gln Asp Glu Trp Thr Glu Leu Ser Met Ala Asp
225                 230                 235                 240
Ile Arg Ala Leu Glu Glu Thr Ala Arg Met Leu Ala Gln Arg Met
            245                 250                 255
Ala Lys Cys Asn Thr Gly Ser Glu Gly Ser Glu Ala Gln Pro Pro Gly
                260                 265                 270
Lys Pro Ser Thr Glu Ala Arg Ser Ala Ala Ser Asn Thr Gly Thr Pro
            275                 280                 285
Asp Gly Pro Glu Ala Pro Pro Gly Pro Asp Ala Ser Pro Asp Ala Ser
        290                 295                 300
Phe Gly Lys Gln Trp Ser Ser Ser Arg Ser Ser Tyr Ser Ser Gln
305                 310                 315                 320
His Gly Gly Ala Val Ser Pro Gln Ser Leu Ser Glu Trp Arg Met Gln
                325                 330                 335
Asn Ile Ala Arg Asp Ser Glu Asn Ser Ser Glu Glu Phe Phe Asp
            340                 345                 350
Ala His Glu Gly Phe Ser Asp Ser Glu Glu Val Phe Pro Lys Glu Met
        355                 360                 365
Thr Lys Trp Asn Ser Asn Asp Phe Ile Asp Ala Phe Ala Ser Pro Val
    370                 375                 380
Glu Ala Glu Gly Thr Pro Glu Pro Gly Ala Glu Ala Lys Gly Ile
385                 390                 395                 400
Glu Asp Gly Ala Gln Ala Pro Arg Asp Ser Glu Gly Leu Asp Gly Ala
                405                 410                 415
Gly Glu Leu Gly Ala Glu Ala Cys Ala Val His Ala Leu Phe Leu Ile
            420                 425                 430
Leu His Ser Gly Asn Ile Leu Asp Ser Gly Pro Gly Asp Ala Asn Ser
        435                 440                 445
```

-continued

```
Lys Gln Ala Asp Val Gln Thr Leu Ser Ser Ala Phe Glu Ala Val Thr
    450                 455                 460
Arg Ile His Phe Pro Glu Ala Leu Gly His Val Ala Leu Arg Leu Val
465                 470                 475                 480
Pro Cys Pro Pro Ile Cys Ala Ala Tyr Ala Leu Val Ser Asn Leu
                    485                 490                 495
Ser Pro Tyr Ser His Asp Gly Asp Ser Leu Ser Arg Ser Gln Asp His
                500                 505                 510
Ile Pro Leu Ala Ala Leu Pro Leu Leu Ala Thr Ser Ser Arg Tyr
            515                 520                 525
Gln Gly Ala Val Ala Thr Val Ile Ala Arg Thr Asn Gln Ala Tyr Ser
        530                 535                 540
Ala Phe Leu Arg Ser Pro Glu Gly Ala Gly Phe Cys Gly Gln Val Ala
545                 550                 555                 560
Leu Ile Gly Asp Gly Val Gly Gly Ile Leu Gly Phe Asp Ala Leu Cys
                565                 570                 575
His Ser Ala Asn Ala Gly Thr Gly Ser Arg Gly Ser Ser Arg Arg Gly
                580                 585                 590
Ser Met Asn Asn Glu Leu Leu Ser Pro Glu Phe Gly Pro Val Arg Asp
            595                 600                 605
Pro Leu Ala Asp Gly Val Glu Gly Leu Gly Arg Gly Ser Pro Glu Pro
        610                 615                 620
Ser Ala Leu Pro Pro Gln Arg Ile Pro Ser Asp Met Ala Ser Pro Glu
625                 630                 635                 640
Pro Glu Gly Ser Gln Asn Ser Leu Gln Ala Ala Pro Ala Thr Thr Ser
                645                 650                 655
Ser Trp Glu Pro Arg Arg Ala Ser Thr Ala Phe Cys Pro Pro Ala Ala
                660                 665                 670
Ser Ser Glu Ala Pro Asp Gly Pro Ser Ser Thr Ala Arg Leu Asp Phe
            675                 680                 685
Lys Val Ser Gly Phe Phe Leu Phe Gly Ser Pro Leu Gly Leu Val Leu
        690                 695                 700
Ala Leu Arg Lys Thr Val Met Pro Ala Leu Glu Ala Ala Gln Met Arg
705                 710                 715                 720
Pro Ala Cys Glu Gln Ile Tyr Asn Leu Phe His Ala Ala Asp Pro Cys
                725                 730                 735
Ala Ser Arg Leu Glu Pro Leu Leu Ala Pro Lys Phe Gln Ala Ile Ala
            740                 745                 750
Pro Leu Thr Val Pro Arg Tyr Gln Lys Phe Pro Leu Gly Asp Gly Ser
        755                 760                 765
Ser Leu Leu Leu Ala Asp Thr Leu Gln Thr His Ser Ser Leu Phe Leu
    770                 775                 780
Glu Glu Leu Glu Met Leu Val Pro Ser Thr Pro Thr Ser Thr Ser Gly
785                 790                 795                 800
Ala Phe Trp Lys Gly Ser Glu Leu Ala Thr Asp Pro Pro Ala Gln Pro
                805                 810                 815
Ala Ala Pro Ser Thr Thr Ser Glu Val Val Lys Ile Leu Glu Arg Trp
            820                 825                 830
Trp Gly Thr Lys Arg Ile Asp Tyr Ser Leu Tyr Cys Pro Glu Ala Leu
        835                 840                 845
Thr Ala Phe Pro Thr Val Thr Leu Pro His Leu Phe His Ala Ser Tyr
    850                 855                 860
```

-continued

```
Trp Glu Ser Ala Asp Val Val Ala Phe Ile Leu Arg Gln Val Ile Glu
865                 870                 875                 880

Lys Glu Arg Pro Gln Leu Ala Glu Cys Glu Pro Ser Ile Tyr Ser
            885                 890                 895

Pro Ala Phe Pro Arg Glu Lys Trp Gln Arg Lys Arg Thr Gln Val Lys
                900                 905                 910

Ile Arg Asn Val Thr Ser Asn His Arg Ala Ser Asp Thr Val Cys
            915                 920                 925

Glu Gly Pro Pro Gln Val Leu Ser Gly Arg Phe Met Tyr Gly Pro Leu
    930                 935                 940

Asp Val Val Thr Leu Thr Gly Glu Lys Val Asp Val Tyr Ile Met Thr
945                 950                 955                 960

Gln Pro Leu Ser Gly Lys Trp Ile His Phe Gly Thr Glu Val Thr Asn
                965                 970                 975

Ser Ser Gly Arg Leu Thr Phe Pro Val Pro Pro Glu Arg Ala Leu Gly
            980                 985                 990

Ile Gly Val Tyr Pro Val Arg Met Val Val Arg Gly Asp His Thr Tyr
            995                 1000                1005

Ala Glu Cys Cys Leu Thr Val Val Ala Arg Gly Thr Glu Ala Val Val
    1010                1015                1020

Phe Ser Ile Asp Gly Ser Phe Thr Ala Ser Val Ser Ile Met Gly Ser
1025                1030                1035                1040

Asp Pro Lys Val Arg Ala Gly Ala Val Asp Val Val Arg His Trp Gln
                1045                1050                1055

Asp Ser Gly Tyr Leu Ile Val Tyr Val Thr Gly Arg Pro Asp Met Gln
            1060                1065                1070

Lys His Arg Val Val Ala Trp Leu Ser Gln His Asn Phe Pro His Gly
    1075                1080                1085

Val Val Ser Phe Cys Asp Gly Leu Thr His Asp Pro Leu Arg Gln Lys
    1090                1095                1100

Ala Met Phe Leu Gln Ser Leu Val Gln Glu Val Glu Leu Asn Ile Val
1105                1110                1115                1120

Ala Gly Tyr Gly Ser Pro Lys Asp Val Ala Val Tyr Ala Ala Leu Gly
            1125                1130                1135

Leu Ser Pro Ser Gln Thr Tyr Ile Val Gly Arg Ala Val Arg Lys Leu
        1140                1145                1150

Gln Ala Gln Cys Gln Phe Leu Ser Asp Gly Tyr Val Ala His Leu Gly
        1155                1160                1165

Gln Leu Glu Ala Gly Ser His Ser His Ala Ser Ser Gly Pro Pro Arg
    1170                1175                1180

Ala Ala Leu Gly Lys Ser Ser Tyr Gly Val Ala Ala Pro Val Asp Phe
1185                1190                1195                1200

Leu Arg Lys Gln Ser Gln Leu Leu Arg Ser Arg Gly Pro Ser Gln Ala
            1205                1210                1215

Glu Arg Glu Gly Pro Gly Thr Pro Pro Thr Thr Leu Ala Arg Gly Lys
            1220                1225                1230

Ala Arg Ser Ile Ser Leu Lys Leu Asp Ser Glu Glu
    1235                1240
```

(2) INFORMATION FOR SEQ ID NO: 6:

(i) SEQUENCE CHARACTERISTICS:
        (A) LENGTH: 1349 amino acids
        (B) TYPE: amino acid
        (C) STRANDEDNESS: single

```
            (D) TOPOLOGY: linear (ii) MOLECULE TYPE: peptide (xi) SEQUENCE DESCRIPTION: SEQ ID NO: 6:

Met Ile Ile Lys Glu Tyr Arg Ile Pro Leu Pro Met Thr Val Glu Glu
 1               5                  10                  15

Tyr Arg Ile Ala Gln Leu Tyr Met Ile Gln Lys Lys Ser Arg Asn Glu
             20                  25                  30

Thr Tyr Gly Glu Gly Ser Gly Val Glu Ile Leu Glu Asn Arg Pro Tyr
         35                  40                  45

Thr Asp Gly Pro Gly Gly Ser Gly Gln Tyr Thr His Lys Val Tyr His
     50                  55                  60

Val Gly Met His Ile Pro Ser Trp Phe Arg Ser Ile Leu Pro Lys Ala
65                  70                  75                  80

Ala Leu Arg Val Val Glu Glu Ser Trp Asn Ala Tyr Pro Tyr Thr Arg
                 85                  90                  95

Thr Arg Phe Thr Cys Pro Phe Val Glu Lys Phe Ser Ile Asp Ile Glu
                100                 105                 110

Thr Phe Tyr Lys Thr Asp Ala Gly Glu Asn Pro Asp Val Phe Asn Leu
            115                 120                 125

Ser Pro Val Glu Lys Asn Gln Leu Thr Ile Asp Phe Ile Asp Ile Val
        130                 135                 140

Lys Asp Pro Val Pro His Asn Glu Tyr Lys Thr Glu Glu Asp Pro Lys
145                 150                 155                 160

Leu Phe Gln Ser Thr Lys Thr Gln Arg Gly Pro Leu Ser Glu Asn Trp
                165                 170                 175

Ile Glu Glu Tyr Lys Lys Gln Val Phe Pro Ile Met Cys Ala Tyr Lys
            180                 185                 190

Leu Cys Lys Val Glu Phe Arg Tyr Trp Gly Met Gln Ser Lys Ile Glu
        195                 200                 205

Arg Phe Ile His Asp Thr Gly Leu Arg Arg Val Met Val Arg Ala His
    210                 215                 220

Arg Gln Ala Trp Cys Trp Gln Asp Glu Trp Tyr Gly Leu Ser Met Glu
225                 230                 235                 240

Asn Ile Arg Glu Leu Glu Lys Glu Ala Gln Leu Met Leu Ser Arg Lys
                245                 250                 255

Met Ala Gln Phe Asn Glu Asp Gly Glu Glu Ala Thr Glu Leu Val Lys
            260                 265                 270

His Glu Ala Val Ser Asp Gln Thr Ser Gly Glu Pro Pro Glu Pro Ser
        275                 280                 285

Ser Ser Asn Gly Glu Pro Leu Val Gly Arg Gly Leu Lys Lys Gln Trp
    290                 295                 300

Ser Thr Ser Ser Lys Ser Ser Arg Ser Ser Lys Arg Gly Ala Ser Pro
305                 310                 315                 320

Ser Arg His Ser Ile Ser Glu Trp Arg Met Gln Ser Ile Ala Arg Asp
                325                 330                 335

Ser Asp Glu Ser Ser Asp Asp Glu Phe Phe Asp Ala His Glu Asp Leu
            340                 345                 350

Ser Asp Thr Glu Glu Met Phe Pro Lys Asp Ile Thr Lys Trp Ser Ser
        355                 360                 365

Asn Asp Leu Met Asp Lys Ile Glu Ser Pro Glu Pro Glu Asp Thr Gln
    370                 375                 380

Asp Gly Leu Tyr Arg Gln Gly Ala Pro Glu Phe Arg Val Ala Ser Ser
```

-continued

```
            385                 390                 395                 400
Val Glu Gln Leu Asn Ile Ile Glu Asp Glu Val Ser Gln Pro Leu Ala
                    405                 410                 415
Ala Pro Pro Ser Lys Ile His Val Leu Leu Val Leu His Gly Gly
                420                 425                 430
Thr Ile Leu Asp Thr Gly Ala Gly Asp Pro Ser Ser Lys Lys Gly Asp
            435                 440                 445
Ala Asn Thr Ile Ala Asn Val Phe Asp Thr Val Met Arg Val His Tyr
        450                 455                 460
Pro Ser Ala Leu Gly Arg Leu Ala Ile Arg Leu Val Pro Cys Pro Pro
465                 470                 475                 480
Val Cys Ser Asp Ala Phe Ala Leu Val Ser Asn Leu Ser Pro Tyr Ser
                485                 490                 495
His Asp Glu Gly Cys Leu Ser Ser Ser Gln Asp His Ile Pro Leu Ala
                500                 505                 510
Ala Leu Pro Leu Leu Ala Thr Ser Ser Pro Gln Tyr Gln Glu Ala Val
            515                 520                 525
Ala Thr Val Ile Gln Arg Ala Asn Leu Ala Tyr Gly Asp Phe Ile Lys
        530                 535                 540
Ser Gln Glu Gly Met Thr Phe Asn Gly Gln Val Cys Leu Ile Gly Asp
545                 550                 555                 560
Cys Val Gly Gly Ile Leu Ala Phe Asp Ala Leu Cys Tyr Ser Asn Gln
                565                 570                 575
Pro Val Ser Glu Ser Gln Ser Ser Arg Arg Gly Ser Val Val Ser
                580                 585                 590
Met Gln Asp Asn Asp Leu Leu Ser Pro Gly Ile Leu Met Asn Ala Ala
            595                 600                 605
His Cys Cys Gly Gly Gly Gly Gly Gly Gly Gly Gly Ser Ser
        610                 615                 620
Gly Gly Gly Gly Ser Ser Gly Gly Ser Ser Leu Glu Ser Ser Arg His
625                 630                 635                 640
Leu Ser Arg Ser Asn Val Asp Ile Pro Arg Ser Asn Gly Thr Glu Asp
                645                 650                 655
Pro Lys Arg Gln Leu Pro Arg Lys Arg Ser Asp Ser Ser Thr Tyr Glu
                660                 665                 670
Leu Asp Thr Ile Gln Gln His Gln Ala Phe Leu Ser Ser Leu His Ala
            675                 680                 685
Ser Val Leu Arg Thr Glu Pro Cys Ser Arg His Ser Ser Ser Ser Thr
        690                 695                 700
Met Leu Asp Gly Thr Gly Ala Leu Gly Arg Phe Asp Phe Glu Ile Thr
705                 710                 715                 720
Asp Leu Phe Leu Phe Gly Cys Pro Leu Gly Leu Val Leu Ala Leu Arg
                725                 730                 735
Lys Thr Val Ile Pro Ala Leu Asp Val Phe Gln Leu Arg Pro Ala Cys
                740                 745                 750
Gln Gln Val Tyr Asn Leu Phe His Pro Ala Asp Pro Ser Ala Ser Arg
            755                 760                 765
Leu Glu Pro Leu Leu Glu Arg Arg Phe His Ala Leu Pro Pro Phe Ser
        770                 775                 780
Val Pro Arg Tyr Gln Arg Tyr Pro Leu Gly Asp Gly Cys Ser Thr Leu
785                 790                 795                 800
Leu Ala Asp Val Leu Gln Thr His Asn Ala Ala Phe Gln Glu His Gly
                805                 810                 815
```

-continued

Ala Pro Ser Ser Pro Gly Thr Ala Pro Ala Ser Arg Gly Phe Arg Arg
            820                 825                 830

Ala Ser Glu Ile Ser Ile Ala Ser Gln Val Ser Gly Met Ala Glu Ser
            835                 840                 845

Tyr Thr Ala Ser Ser Ile Ala Gln Lys Ala Pro Asp Ala Leu Ser His
            850                 855                 860

Thr Pro Ser Val Arg Arg Leu Ser Leu Ala Leu Pro Ala Pro Ser
865                 870                 875                 880

Pro Thr Thr Pro Gly Pro His Pro Ala Arg Lys Ala Ser Pro Gly
                885                 890                 895

Leu Glu Arg Ala Pro Gly Leu Pro Glu Leu Asp Ile Gly Glu Val Ala
            900                 905                 910

Ala Lys Trp Trp Gly Gln Lys Arg Ile Asp Tyr Ala Leu Tyr Cys Pro
            915                 920                 925

Asp Ala Leu Thr Ala Phe Pro Thr Val Ala Leu Pro His Leu Phe His
            930                 935                 940

Ala Ser Tyr Trp Glu Ser Thr Asp Val Val Ser Phe Leu Leu Arg Gln
945                 950                 955                 960

Val Met Arg His Asp Asn Ser Ser Ile Leu Glu Leu Asp Gly Lys Glu
            965                 970                 975

Val Ser Val Phe Thr Pro Ser Lys Pro Arg Glu Lys Trp Gln Arg Lys
            980                 985                 990

Arg Thr His Val Lys Leu Arg Asn Val Thr Ala Asn His Arg Ile Asn
            995                 1000                1005

Asp Ala Leu Ala Asn Glu Asp Gly Pro Gln Val Leu Thr Gly Arg Phe
    1010                1015                1020

Met Tyr Gly Pro Leu Asp Met Val Thr Leu Thr Gly Glu Lys Val Asp
1025                1030                1035                1040

Val His Ile Met Thr Gln Pro Pro Ser Gly Glu Trp Leu Tyr Leu Asp
                1045                1050                1055

Thr Leu Val Thr Asn Asn Ser Gly Arg Val Ser Tyr Thr Ile Pro Glu
            1060                1065                1070

Ser His Arg Leu Gly Val Gly Val Tyr Pro Ile Lys Met Val Val Arg
            1075                1080                1085

Gly Asp His Thr Phe Ala Asp Ser Tyr Ile Thr Val Leu Pro Lys Gly
    1090                1095                1100

Thr Glu Phe Val Val Phe Ser Ile Asp Gly Ser Phe Ala Ala Ser Val
1105                1110                1115                1120

Ser Ile Met Gly Ser Asp Pro Lys Val Arg Ala Gly Ala Val Asp Val
            1125                1130                1135

Val Arg His Trp Gln Asp Leu Gly Tyr Leu Ile Ile Tyr Val Thr Gly
            1140                1145                1150

Arg Pro Asp Met Gln Lys Gln Arg Val Val Ala Trp Leu Ala Gln His
    1155                1160                1165

Asn Phe Pro His Gly Val Val Ser Phe Cys Asp Gly Leu Val His Asp
    1170                1175                1180

Pro Leu Arg His Lys Ala Asn Phe Leu Lys Leu Leu Ile Ser Glu Leu
1185                1190                1195                1200

His Leu Arg Val His Ala Ala Tyr Gly Ser Thr Lys Asp Val Ala Val
                1205                1210                1215

Tyr Ser Ala Ile Ser Leu Ser Pro Met Gln Ile Tyr Ile Val Gly Arg
    1220                1225                1230

```
Pro Thr Lys Lys Leu Gln Gln Gln Cys Gln Phe Ile Thr Asp Gly Tyr
        1235                1240                1245

Ala Ala His Leu Ala Gln Leu Lys Tyr Ser His Arg Ala Arg Pro Ala
        1250                1255                1260

Arg Asn Thr Ala Thr Arg Met Ala Leu Arg Lys Gly Ser Phe Gly Leu
1265                1270                1275                1280

Pro Gly Gln Gly Asp Phe Leu Arg Ser Arg Asn His Leu Leu Arg Thr
                1285                1290                1295

Ile Ser Ala Gln Pro Ser Gly Pro Ser His Arg His Glu Arg Thr Gln
        1300                1305                1310

Ser Gln Ala Asp Gly Glu Gln Arg Gly Gln Arg Ser Met Ser Val Ala
        1315                1320                1325

Ala Gly Cys Trp Gly Arg Ala Met Thr Gly Arg Leu Glu Pro Gly Ala
        1330                1335                1340

Ala Ala Gly Pro Lys
1345

(2) INFORMATION FOR SEQ ID NO: 7:

(i) SEQUENCE CHARACTERISTICS:
        (A) LENGTH: 986 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Met Leu Ile Lys Glu Tyr Arg Ile Leu Pro Met Thr Val Gln Glu
1                5                10               15

Tyr Arg Ile Ala Gln Leu Tyr Met Ile Gln Lys Lys Ser Arg Leu Asp
                20                25                30

Ser His Gly Gln Asp Ser Gly Val Glu Ile Ile Ser Asn Lys Pro Tyr
        35                40                45

Thr Asp Gly Pro Gly Gly Ser Gly Gln Tyr Thr Phe Lys Ile Tyr His
        50                55                60

Ile Gly Ser Arg Ile Pro Ala Trp Ile Arg Thr Val Leu Pro Thr Asn
65               70                75                80

Ala Leu Glu Ala His Glu Glu Ser Trp Asn Ala Tyr Pro Val Thr Lys
                85                90                95

Thr Arg Tyr Ser Thr Pro Met Met Arg Phe Ser Leu Glu Val Glu
                100               105               110

Thr Leu Tyr Phe Asp His Gly Gln Gln Glu Asn Val Phe Asn Leu
        115               120               125

Asn Glu Lys Asp Lys Ser Thr Arg Ile Ile Asp Tyr Met Asp Phe Val
        130               135               140

Lys Asp Pro Ile Ser Ser His Asp Tyr Cys Ala Glu Asp Pro Lys
145               150               155               160

Leu Tyr Arg Ser Glu Thr Thr Asn Arg Gly Pro Leu Asn Asp Asp Trp
                165               170               175

Val Ala Glu His Leu Lys Lys Gly Leu Pro Ile Met Cys Ala Tyr Lys
        180               185               190

Leu Cys Lys Val Glu Phe Arg Tyr Trp Gly Met Gln Thr Arg Ala Glu
        195               200               205

Arg Trp Ile His Asp Leu Ala Leu Arg Asn Thr Met Met Arg Ala His
        210               215               220
```

```
Arg Gln Ala Trp Ala Trp Gln Asp Glu Trp Thr Gly Leu Thr Met Asn
225                 230                 235                 240

Asp Ile Arg Lys Leu Glu Ala Glu Ala Leu His Leu Ser Lys Val
            245                 250                 255

Met Ser Val Lys Glu Asn Glu Asp Gly His Gln Asp Glu Asn Asp Thr
            260                 265                 270

Asp Asp Asp Met Asp Ala Gly Asp Ala Val Ser Asp Leu Tyr Phe
            275                 280                 285

Asp Cys Thr Asp Thr Ser Pro Ile Pro Thr Gln Lys Pro Ser Ile Ile
            290                 295                 300

Arg Trp Ser Ser Glu Leu Glu Leu Glu Ile Gln Asp Asp Asn Ser Pro
305                 310                 315                 320

Pro Leu Thr Pro His Asn Gly Ser Thr Glu Val Ala Leu Leu Ile Met
                325                 330                 335

Val Phe His Gly Asp Phe Ser Pro Asp Asn Pro Ala Asp Ser Lys Thr
                340                 345                 350

Thr Asp Thr Asn Thr Phe Ser Ser Thr Ile Glu Thr Cys Val Gln Arg
            355                 360                 365

His Tyr Pro Gln Leu Arg Asn Arg Leu His Ile Val Asn Val Ser Cys
370                 375                 380

Gly His Glu Met Thr Gln Val Val Ser Lys Leu Ser Asn Ile Ser Pro
385                 390                 395                 400

Ser Phe Gly Leu Leu His Pro Ser Leu Ser Leu Met Leu Pro Ser Ala
                405                 410                 415

Ser His Leu Tyr Asn Glu Ala Val Glu Gly Thr Ile Arg Arg Ala Asn
                420                 425                 430

Glu Thr Tyr Asn Glu Phe Ile Ala Ser Gln Pro Leu Phe Asn Gly Glu
            435                 440                 445

Val Phe Val Val Gly Asp Cys Val Gly Gly Ile Phe Leu Tyr Glu Ala
    450                 455                 460

Met Thr Arg Lys Cys Asp Ser Met Thr Leu Leu Lys Arg Leu Ser Ser
465                 470                 475                 480

Asn Leu Ser Ser Arg Ile Ile Lys Glu Asp Gln Ser Pro His Gln Ser
                485                 490                 495

Met Thr Asp Ile Thr Ile Thr Asp Thr Ser Ser Ile Ser Ser Cys Pro
            500                 505                 510

Gln Gln His Asn Gln Ser Val Arg Asp His Ser Ser Leu Gln Asn Gly
            515                 520                 525

His Ala Ser Arg Arg Ser Ala Arg Asn Tyr Ser Ala Pro Pro Ser Ala
530                 535                 540

Ser Tyr Val Gln Ile Asp Gly Leu Asp Ser Cys Gln Leu Phe Asn Leu
545                 550                 555                 560

Tyr Tyr Pro Leu Asp Pro Cys Gly Ala Arg Ile Glu Pro Val Leu Asp
                565                 570                 575

Gly Gln Leu Ser Cys Val Pro Pro Tyr Asn Val Pro Lys Tyr Pro Leu
            580                 585                 590

Gly Asp Gly Lys Ser Gln Lys Phe Glu Ser Thr Ile Asp Ala Thr Gln
            595                 600                 605

Met Trp Gly Ser Lys Arg Ile Asp Asn Leu Tyr Cys Pro Asn Ser
            610                 615                 620

Met Val Val Ala Leu Pro Ser Ser Ala Leu Pro Asn Ile Leu His Ala
625                 630                 635                 640

Ser Tyr Trp Glu Ser Cys Asp Val Ala Ser Phe Leu Leu Arg Gln Phe
```

```
                    645             650             655
Val Arg Gly Glu Glu Asn Ser Val Leu Thr Thr Leu Ser Ser Ser Met
            660             665             670

Asn Asn Ile Pro Leu Asn Ile Asp Leu Pro Thr Met His Trp Lys Arg
            675             680             685

Lys Arg Thr Arg Phe Lys Ile Ala Asn Leu Ser Ala Asn His Arg Ala
            690             695             700

Asn Asp Ile Leu Val Thr Ala Gly Met Asp Leu Thr Val Ile Ala Lys
705             710             715             720

Phe Cys Tyr Gly Pro Met Asp Leu Val Ala Leu Ser Arg Glu Pro Val
                725             730             735

Ser Val Phe Val Tyr Pro Gln Arg Gly Asp Trp Tyr Leu His Gly Val
            740             745             750

Phe Asp Thr Asp Ser His Gly Arg Leu Thr Leu Gln Leu Ala Lys Thr
            755             760             765

Leu Pro Cys Gly Ile His Ser Val Lys Ile Val His Gly Asp Arg
    770             775             780

Ser Tyr Leu Asp Ala Phe Val Ala Ile Val Pro His Gly Thr Lys Cys
785             790             795             800

Ala Val Phe Ser Val Asp Gly Ser Leu Thr Ala Ser Val Ser Val Thr
                805             810             815

Gly Lys Asp Pro Arg Val Arg Pro Gly Ala Val Asp Val Val Arg Tyr
            820             825             830

Trp Gln Glu Gln Gly Tyr Leu Ile Ile Tyr Leu Thr Ala Arg Pro Asp
            835             840             845

Met Gln Gln Arg Val Val Ser Ala Trp Leu Ala Gln His Asn Phe Pro
850             855             860

His Ala Leu Leu Phe Phe Asn Asn Ser Phe Ser Thr Glu Pro Leu Lys
865             870             875             880

Gln Lys Ser Leu His Leu Arg His Ile Val Asp Met Gly Val His Ile
                885             890             895

His Val Ala Tyr Gly Ser Gly Lys Asp Val Asn Val Tyr Thr Ser Ala
            900             905             910

Gly Val Asp Pro Glu His Val Ile Ser Val Ala Gly Ser Arg Arg Arg
            915             920             925

Asn Cys Val Gln Ile Glu Ser Tyr Ser Ser His Leu Ala Ala Leu Asn
930             935             940

Ser Gly Gln Cys Thr Leu Gly Lys Arg Ile Glu Asp Gly Leu Thr
945             950             955             960

Leu Gln Leu His Arg Asn Val Gln Arg Thr Pro Ser Phe Thr Pro Arg
                965             970             975

Gly Gly Lys Phe Glu Asn Glu Lys Asp Arg
            980             985
```

(2) INFORMATION FOR SEQ ID NO: 8:

(i) SEQUENCE CHARACTERISTICS:
        (A) LENGTH: 4308 base pairs
        (B) TYPE: nucleic acid
        (C) STRANDEDNESS: single
        (D) TOPOLOGY: linear (xi) SEQUENCE DESCRIPTION: SEQ ID NO: 8:

```
GCGGCCGCCA CAAACAAACA AACACACGGA CACACATCTG GACCTGTACA CCTACGGCCC    60

CGGAAAATTA TCCATAGAAC AACCGCTGAC TGACCCCGCC TCGTTTTTTC CAATTCCATC   120
```

```
ATTCCGACCA GGTCATAGAC GACGTGCCGC CACCCCACGC CAATCACCCC CCTCGCCACA    180

AAAAACGAAA AAAAAAACCG TCGGACGACA GCCACGTCGC GCCTTCACAT CATCCAGCCA    240

TGACCAGCGG CGGCAATCGA TGATTGCCAT TCCCTCAGCC AACGAGAGCC AATAGAGGCA    300

GCCGGAAAGG AGGACGCCGG AATAGTCAGT CGGTATCGTC GGAAGAGTGC GCCATTCGCA    360

GAACGTCAAT AGCCGGAGGG GAGTCCGCCA TTTCAACGAC AAGGACCCAA GTCACGCGGT    420

GTCAACATGC TGATCAAGGA GTACCGCATT CCGCTGCCCC TCACCGTCGA GGAGTACCGC    480

ATCGCCCAGC TCTACATGAT TGCGAAAAAG AGTCGCGAGG AGAGCCATGG CGAGGGCAGT    540

GGCGTTGAGA TAATCATCAA TGAGCCGTAC AAGGATGGAC CCGGCGGTAA TGGTCAATAC    600

ACAAAGAAGA TCTATCACGT GGGCAATCAT CTGCCTGGCT GGATTAAAAG TCTCTTGCCG    660

AAAAGCGCTT TAACCGTGGA GGAGGAGGCC ATGGAATGCT ATCCGTATAC CAGGACTCGC    720

TACACCTGTC CGTTTGTGGA GAAATTCTCG CTGGATATTG AGACATACTA TTATCCGGAC    780

AATGGCTATC AGGACAATGT CTTCCAGCTG TCCGGAAGCG ATTTGCGTAA TCGGATCGTA    840

GACGTAATTG ACATTGTCAA GGATCAGCTG TGGGGCGGTG ACTATGTGAA GGAGGAGGAT    900

CCCAAGCACT TTGTGTCGGA CAAGACGGGC CGTGGACCCT GGCCGAGGA TTGGCTGGAG     960

GAGTATTGGC GCGAAGTGAA GGGCAAAAAG CAACCGACAC CGCGCAACAT GTCCCTGATG   1020

ACCGCCTACA AGATCTGCCG CGTGGAGTTT CGCTACTGGG GCATGCAGAC AAAGCTGGAG   1080

AAGTTCATCC ACGATGTGGC GCTGCGCAAG ATGATGCTGC GGGCCCATCG CAGGCGTGG    1140

GCATGGCAGG ACGAGTGGTT CGGCTTGACC ATCGAGGATA TACGCGAGCT GGAGCGACAG   1200

ACGCAACTGG CCCTGGCCAA GAAAATGGGC GGCGGCGAGG AGTGCAGCGA CGACAGCGTC   1260

TCGGAGCCGT ATGTCAGCAC GGCGGCCACC GCCGCATCCA CAACGGGCAG CGAGCGAAAG   1320

AAGTCCGCTC CGGCTGTGCC GCCTATTGTC ACCCAGCAGC CGCCGAGCGC CGAGGCCAGT   1380

TCGGATGAGG AGGGCGAGGA GGAGGAGGAT GACGACGAGG ACGAGAACGA TGCCATTGGC   1440

ACGGGCGTGG ATCTGTCAGC CAACCAAGGC GGATCCGCGC AGCGCTCGCG CTCCCAAAGC   1500

ATTCAAATGG CCCAGAAGGG CAAGTTCGGT TCAAAGGGTG CCCTTCACTC GCCGGTGGGA   1560

TCTGCCCATA GCTTCGATCT CCAGGTGGCT AACTGGCGTA TGGAGCGATT GGAAGTGGAC   1620

TCCAAATCCA ATTCGGATGA GGAATTCTTT GATTGCCTGG ACACCAATGA GACGAACTCG   1680

CTGGCCAAGT GGAGCTCGCT GGAGCTGCTT GGCGAGGGCG ACGACAGTCC GCCGCCACAT   1740

GGCGGACCCT CTAGTGCAGC ATCGGTGGGT GGGCGTGGCA ACTCGCGGCA AGAGGACAGC   1800

ATATTCAATC AGGACTTTCT GATGCGCGTG GCCTCGGAGC GCGGCAACAA GCGGCAGTTA   1860

CGTTCCTCGG CCAGCGTGGA TCGCAGTCAC GATTCATCGC CGCCGGGATC GCCGAGTACA   1920

CCGTCGTGTC CCACAACCAT TCTGATCCTG GTTGTCCATG CGGGCAGCGT TTTGGATGCG   1980

GCCAGCGAGC TGACCGCCAA GAAATCCGAT GTGACCACAT TCCGTGGCTC CTTCGAGGCG   2040

GTTATGCGAC ACGACTATCC CAGCCTCCTC ACCCATGTGA CCATCAAGAT GGTGCCGTGC   2100

CCCTCAATAT GCACCGACGC CCTGGGCATT CTCTCCAGCC TGAGTCCGTA CTCCTTTGAT   2160

GCGTCGCCCT CGGCGGCGGA TATACCGAAT ATAGCCGATG TCCCCATTGG AGCTATACCA   2220

CTACTATCTG TGGCATCGCC AGAATTCCAC GAGACGGTCA ACAAGACGGT TGCCGCTGCC   2280

AATATTGTCT GCCATGAGTT TTTGAAATCG GAGGAGGGTC ACGGATTCTC TGGCCAGATT   2340

GTCATGCTGG GCGATTCGAT GGGTTCGCTG CTGGCGTACG AGGCCCTCTG CCGATCGAAT   2400

GGCAGCCAGC CGGGCACGGC TTCGGGTGCC TCGAATTCCG GCGGAGATGC GGCCACAAAT   2460
```

-continued

```
ATAAATACCC ACAATCCGTT GAGCCCACGT AATTCGCGAT TGGACGATGA CGAGCGTTTC    2520

ATCGAAGCCG ATCTGGATGC CAAGCGTTTG CTAGTGGCCC CATCGCCACG TAGACGCCGT    2580

TCCAGCTCAT CCAGCGATTC GCGTGCCACC AAATTGGACT TTGAGGTCTG TGACTTCTTC    2640

ATGTTCGGAT CGCCGCTATC TGTGGTGCTG GCTGCAAGGA AACTTCACGA TGCCAAGGCC    2700

GCCCTGCCGC GGCCCAACTG CCACCAGGTC TACAATCTGT TCCATCCAAC CGATCCGATC    2760

GCCTCGCGCC TGGAGCCGCT TCTGAGCGCC CGGTTTTCTA TATTGGCGCC AGTCAATGTC    2820

CCACGGTACG CCAAGTATCC GCTGGGTAAT GGACAGCCAT TGCATTTATT GGAGGTCATT    2880

CAATCGCATC CGCAGCGCTT TAACGATGGC AATAACCTAT TGGCTGGTCG CCGTTTGTCG    2940

GACGCATCCA TGCAGAGCAC GATATCGGGT CTGATTGAGA ATGTCTCGCT TAGTACGATC    3000

CATGCCCTGC AAAACAAATG GTGGGGCACA AAGCGCTTGG ATTACGCATT ATATTGCCCG    3060

GAGGGATTGA GTAATTTCCC TGCTCACGCC TTGCCGCACC TCTTCCATGC CAGCTACTGG    3120

GAGAGTCCGG ATGTGATTGC CTTTATTCTA CGGCAGATTG CAAATTCGA GGGCATACCC    3180

TTTGTGGGCT CAAACGATGA CAAGGACAAT GCCTCCTTCC ATCCCGGACA GCCGAGGGAG    3240

AAGTGGATTA AGAAACGGAC CTCGGTTAAG CTGAAAAATG TAGCCGCCAA TCATCGGGCC    3300

AACGATGTAA TCGTGCAGGA GGGCAGGGAG CAGCGATTGA ATGCGAGATT TATGTACGGA    3360

CCCCTGGACA TGATCACGCT GCACGGTGAA AAGGTGGATG TGCACATTAT GAAGGATCCG    3420

CCGGCGGGGC AGTGGACATT CCTCAGCACC GAGGTGACGG ACAAGAATGG TCGCATCTCG    3480

TACAGCATTC CGGATCAGGT ATCCCTTGGC TATGGTATAT ATCCGGTTAA GATGGTGGTC    3540

CGTGGCGATC ACACCTCGGT GGATTGCTAT ATGGCGGTGG TGCCGCGTTA ACCGAATGCG    3600

TGGTCTTCAG CATTGATGGC TCATTCACCG CTTCGATGTC GGTGACAGGT AGGGATCCA    3660

AGGTGCGTGC CGGAGCTGTC GATGTTTGCC GCCACTGGCA GGAGCTGGGC TACCTGCTCA    3720

TTTACATCAC CGGACGACCG GATATGCAGC AGCAACGCGT GGTGTCCTGG CTGAGCCAGC    3780

ACAACTTCCC GCACGGCCTG ATCTCGTTCG CCGACGGCCT GTCCACCGAT CCATTGGGCC    3840

ACAAGACGGC CTATCTCAAC AATTTGGTTC AGAACCATGG AATCTCAATT ACTGCCCGTA    3900

CGGCAGCAGC AAGGACATTA GTGTCTACAC GAATGTTGGC ATGCGAACCG ATCAAATTTT    3960

CATCGTGGGC AAGGTTGGCA AGAAGCTGCA GTCGAATGCC ACCGTGCTTA GCGATGGCTA    4020

TGCCGCCCAC TTGGCCGGTT TGCAGGCTGT GGGTGGTTCG CGTCCGGCGA AGGGCAATGC    4080

CCGCATGGTC ATTCCACGCG GATGCTTCAA TCTTCCCGGC CAGACCGCAA ATCCGCGGCG    4140

CAGAAGGCTG CATGAACAAG CAACGAATGA AAATTGAATT GCAACTCAAG CAAACCAATT    4200

GTTTAGAGCA ATGAAAAACA ACAATTAAAG CGCTTGTAAA CAGATAGAAG ACGTTAAAAC    4260

CAAAAACAAA ACATTACAGA CAATTGATGT TAGAATTAGT GTTCTAGA              4308
```

(2) INFORMATION FOR SEQ ID NO: 9:

(i) SEQUENCE CHARACTERISTICS:
        (A) LENGTH: 1250 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
Met Leu Ile Lys Glu Tyr Arg Ile Pro Leu Pro Leu Thr Val Glu Glu
 1               5                  10                  15

Tyr Arg Ile Ala Gln Leu Tyr Met Ile Ala Lys Lys Ser Arg Glu Glu
```

```
              20                  25                  30
Ser His Gly Glu Gly Ser Gly Val Glu Ile Ile Ile Asn Glu Pro Tyr
        35                  40                  45

Lys Asp Gly Pro Gly Gly Asn Gly Gln Tyr Thr Lys Lys Ile Tyr His
 50                  55                  60

Val Gly Asn His Leu Pro Gly Trp Ile Lys Ser Leu Leu Pro Lys Ser
 65                  70                  75                  80

Ala Leu Thr Val Glu Glu Ala Met Glu Cys Tyr Pro Tyr Thr Arg
                 85                  90                  95

Thr Arg Tyr Thr Cys Pro Phe Val Glu Lys Phe Ser Leu Asp Ile Glu
               100                 105                 110

Thr Tyr Tyr Pro Asp Asn Gly Tyr Gln Asp Asn Val Phe Gln Leu
           115                 120                 125

Ser Gly Ser Asp Leu Arg Asn Arg Ile Val Asp Val Ile Asp Ile Val
           130                 135                 140

Lys Asp Gln Leu Trp Gly Asp Tyr Val Lys Glu Asp Pro Lys
145                 150                 155                 160

His Phe Val Ser Asp Lys Thr Gly Arg Gly Pro Leu Ala Glu Asp Trp
               165                 170                 175

Leu Glu Glu Tyr Trp Arg Glu Val Lys Gly Lys Gln Pro Thr Pro
               180                 185                 190

Arg Asn Met Ser Leu Met Thr Ala Tyr Lys Ile Cys Arg Val Glu Phe
           195                 200                 205

Arg Tyr Trp Gly Met Gln Thr Lys Leu Glu Lys Phe Ile His Asp Val
           210                 215                 220

Ala Leu Arg Lys Met Met Leu Arg Ala His Arg Gln Ala Trp Ala Trp
225                 230                 235                 240

Gln Asp Glu Trp Phe Gly Leu Thr Ile Glu Asp Ile Arg Glu Leu Glu
               245                 250                 255

Arg Gln Thr Gln Leu Ala Leu Ala Lys Lys Met Gly Gly Gly Glu Glu
           260                 265                 270

Cys Ser Asp Asp Ser Val Ser Glu Pro Tyr Val Ser Thr Ala Ala Thr
           275                 280                 285

Ala Ala Ser Thr Thr Gly Ser Glu Arg Lys Lys Ser Ala Pro Ala Val
290                 295                 300

Pro Pro Ile Val Thr Gln Gln Pro Pro Ser Ala Glu Ala Ser Ser Asp
305                 310                 315                 320

Glu Glu Gly Glu Glu Glu Asp Asp Glu Asp Glu Asn Asp Ala
               325                 330                 335

Ile Gly Thr Gly Val Asp Leu Ser Ala Asn Gln Gly Gly Ser Ala Gln
           340                 345                 350

Arg Ser Arg Ser Gln Ser Ile Gln Met Ala Gln Lys Gly Lys Phe Gly
           355                 360                 365

Ser Lys Gly Ala Leu His Ser Pro Val Gly Ser Ala His Ser Phe Asp
           370                 375                 380

Leu Gln Val Ala Asn Trp Arg Met Glu Arg Leu Glu Val Asp Ser Lys
385                 390                 395                 400

Ser Asn Ser Asp Glu Glu Phe Phe Asp Cys Leu Asp Thr Asn Glu Thr
               405                 410                 415

Asn Ser Leu Ala Lys Trp Ser Ser Leu Glu Leu Leu Gly Glu Gly Asp
           420                 425                 430

Asp Ser Pro Pro His Gly Gly Pro Ser Ser Ala Ala Ser Val Gly
           435                 440                 445
```

```
Gly Arg Gly Asn Ser Arg Gln Glu Asp Ser Ile Phe Asn Gln Asp Phe
450                 455                 460

Leu Met Arg Val Ala Ser Glu Arg Gly Asn Lys Arg Gln Leu Arg Ser
465                 470                 475                 480

Ser Ala Ser Val Asp Arg Ser His Asp Ser Ser Pro Pro Gly Ser Pro
                485                 490                 495

Ser Thr Pro Ser Cys Pro Thr Thr Ile Leu Ile Leu Val Val His Ala
            500                 505                 510

Gly Ser Val Leu Asp Ala Ala Ser Glu Leu Thr Ala Lys Lys Ser Asp
        515                 520                 525

Val Thr Thr Phe Arg Gly Ser Phe Glu Ala Val Met Arg His Asp Tyr
    530                 535                 540

Pro Ser Leu Leu Thr His Val Thr Ile Lys Met Val Pro Cys Pro Ser
545                 550                 555                 560

Ile Cys Thr Asp Ala Leu Gly Ile Leu Ser Ser Leu Ser Pro Tyr Ser
                565                 570                 575

Phe Asp Ala Ser Pro Ser Ala Ala Asp Ile Pro Asn Ile Ala Asp Val
            580                 585                 590

Pro Ile Gly Ala Ile Pro Leu Leu Ser Val Ala Ser Pro Glu Phe His
        595                 600                 605

Glu Thr Val Asn Lys Thr Val Ala Ala Asn Ile Val Cys His Glu
    610                 615                 620

Phe Leu Lys Ser Glu Glu Gly His Gly Phe Ser Gly Gln Ile Val Met
625                 630                 635                 640

Leu Gly Asp Ser Met Gly Ser Leu Leu Ala Tyr Glu Ala Leu Cys Arg
                645                 650                 655

Ser Asn Gly Ser Gln Pro Gly Thr Ala Ser Gly Ala Ser Asn Ser Gly
            660                 665                 670

Gly Asp Ala Ala Thr Asn Ile Asn Thr His Asn Pro Leu Ser Pro Arg
        675                 680                 685

Asn Ser Arg Leu Asp Asp Glu Arg Phe Ile Glu Ala Asp Leu Asp
690                 695                 700

Ala Lys Arg Leu Leu Val Ala Pro Ser Pro Arg Arg Arg Ser Ser
705                 710                 715                 720

Ser Ser Ser Asp Ser Arg Ala Thr Lys Leu Asp Phe Glu Val Cys Asp
                725                 730                 735

Phe Phe Met Phe Gly Ser Pro Leu Ser Val Val Leu Ala Ala Arg Lys
            740                 745                 750

Leu His Asp Ala Lys Ala Ala Leu Pro Arg Pro Asn Cys His Gln Val
        755                 760                 765

Tyr Asn Leu Phe His Pro Thr Asp Pro Ile Ala Ser Arg Leu Glu Pro
    770                 775                 780

Leu Leu Ser Ala Arg Phe Ser Ile Leu Ala Pro Val Asn Val Pro Arg
785                 790                 795                 800

Tyr Ala Lys Tyr Pro Leu Gly Asn Gly Gln Pro Leu His Leu Leu Glu
                805                 810                 815

Val Ile Gln Ser His Pro Gln Arg Phe Asn Asp Gly Asn Leu Leu
            820                 825                 830

Ala Gly Arg Arg Leu Ser Asp Ala Ser Met Gln Ser Thr Ile Ser Gly
        835                 840                 845

Leu Ile Glu Asn Val Ser Leu Ser Thr Ile His Ala Leu Gln Asn Lys
850                 855                 860
```

```
Trp Trp Gly Thr Lys Arg Leu Asp Tyr Ala Leu Tyr Cys Pro Glu Gly
865                 870                 875                 880

Leu Ser Asn Phe Pro Ala His Ala Leu Pro His Leu Phe His Ala Ser
            885                 890                 895

Tyr Trp Glu Ser Pro Asp Val Ile Ala Phe Ile Leu Arg Gln Ile Gly
                900                 905                 910

Lys Phe Glu Gly Ile Pro Phe Val Gly Ser Asn Asp Lys Asp Asn
        915                 920                 925

Ala Ser Phe His Pro Gly Gln Pro Arg Glu Lys Trp Ile Lys Lys Arg
        930                 935                 940

Thr Ser Val Lys Leu Lys Asn Val Ala Ala Asn His Arg Ala Asn Asp
945                 950                 955                 960

Val Ile Val Gln Glu Gly Arg Glu Gln Arg Leu Asn Ala Arg Phe Met
                965                 970                 975

Tyr Gly Pro Leu Asp Met Ile Thr Leu His Gly Glu Lys Val Asp Val
            980                 985                 990

His Ile Met Lys Asp Pro Pro Ala Gly Gln Trp Thr Phe Leu Ser Thr
        995                 1000                1005

Glu Val Thr Asp Lys Asn Gly Arg Ile Ser Tyr Ser Ile Pro Asp Gln
    1010                1015                1020

Val Ser Leu Gly Tyr Gly Ile Tyr Pro Val Lys Met Val Val Arg Gly
1025                1030                1035                1040

Asp His Thr Ser Val Asp Cys Tyr Met Ala Val Val Pro Pro Leu Thr
                1045                1050                1055

Glu Cys Val Val Phe Ser Ile Asp Gly Ser Phe Thr Ala Ser Met Ser
            1060                1065                1070

Val Thr Gly Arg Asp Pro Lys Val Arg Ala Gly Ala Val Asp Val Cys
        1075                1080                1085

Arg His Trp Gln Glu Leu Gly Tyr Leu Leu Ile Tyr Ile Thr Gly Arg
        1090                1095                1100

Pro Asp Met Gln Gln Gln Arg Val Val Ser Trp Leu Ser Gln His Asn
1105                1110                1115                1120

Phe Pro His Gly Leu Ile Ser Phe Ala Asp Gly Leu Ser Thr Asp Pro
            1125                1130                1135

Leu Gly His Lys Thr Ala Tyr Leu Asn Asn Leu Val Gln Asn His Gly
        1140                1145                1150

Ile Ser Ile Thr Ala Ala Tyr Gly Ser Ser Lys Asp Ile Ser Val Tyr
        1155                1160                1165

Thr Asn Val Gly Met Arg Thr Asp Gln Ile Phe Ile Val Gly Lys Val
    1170                1175                1180

Gly Lys Lys Leu Gln Ser Asn Ala Thr Val Leu Ser Asp Gly Tyr Ala
1185                1190                1195                1200

Ala His Leu Ala Gly Leu Gln Ala Val Gly Gly Ser Arg Pro Ala Lys
            1205                1210                1215

Gly Asn Ala Arg Met Val Ile Pro Arg Gly Cys Phe Asn Leu Pro Gly
            1220                1225                1230

Gln Thr Ala Asn Pro Arg Arg Arg Arg Leu His Glu Gln Ala Thr Asn
        1235                1240                1245

Glu Asn
    1250

(2) INFORMATION FOR SEQ ID NO: 10:

(i) SEQUENCE CHARACTERISTICS:
```

-continued

```
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Tyr Pro Tyr Asp Val Pro Asp Tyr Ala Ser
1               5                   10

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Glu Gln Lys Leu Ile Ser Glu Glu Asp Leu
1               5                   10
```

Other embodiments are within the following claims.

What is claimed is:

1. An isolated or purified retinal degeneration B (rdgB) polypeptide comprising the full length amino acid sequence set forth in SEQ ID NO: 4, SEQ ID NO: 5, or SEQ ID NO: 6.

2. An isolated or purified rdgB polypeptide having the full amino acid sequence of the sequence set forth in SEQ ID NO: 4 except that it lacks at least one of the following segments of amino acid residues: 1–616 or 616–974.

3. An isolated or purified rdgB polypeptide comprising:
   (a) an amino acid sequence set forth in SEQ ID NO: 4 selected from at least one of the segments of amino acid residues 1–616 or 616–974;
   (b) an amino acid sequence set forth in SEQ ID NO: 5 selected from at least one of the segments of amino acid residues 1–250, 250–900, or 900–1243; or
   (c) an amino acid sequence set forth in SEQ ID NO: 6 selected from at least one of the segments of amino acid residues 1–251, 251–985, or 985–1349.

4. An isolated or purified rdgB polypeptide comprising the full length amino acid sequence set forth in SEQ ID NO: 4 except that it lacks at least one, but not more than two, of the domains selected from the group consisting of the PIT domain, the central domain, the PYK2 binding domain, the calcium binding domain and the nucleotide binding domain.

5. The polypeptide of claim 1, wherein said polypeptide is encoded by the nucleotide sequence of SEQ ID NO: 1.

6. The polypeptide of claim 1, wherein said polypeptide is encoded by the nucleotide sequence of SEQ ID NO: 2.

7. The polypeptide of claim 1, wherein said polypeptide is encoded by the nucleotide sequence of SEQ ID NO: 3.

8. An isolated, or purified rdgB polypeptide comprising at least 20 contiguous amino acids of the polypeptide depicted in SEQ ID NO: 4, SEQ ID NO: 5 or SEQ ID NO: 6.

9. An isolated, or purified rdgB polypeptide comprising at least 30 contiguous amino acids of the polypeptide depicted in SEQ ID NO: 4, SEQ ID NO: 5 or SEQ ID NO: 6.

10. An isolated or purified rdgB polypeptide comprising the full length sequence set forth in SEQ ID NO: 5 except that it lacks at least one, but not all, of the following segments of amino acid residues: 1–250, 250–900, or 900–1243.

11. An isolated or purified rdgB polypeptide comprising the full length sequence set forth in SEQ ID NO: 6 except that it lacks at least one, but not all, of the following segments of amino acid residues: 1–251, 251–985, or 985–1349.

12. An isolated or purified rdgb polypeptide comprising the full length sequence set forth in SEQ ID NO: 5 except that it lacks at least one, but not more than two, of the domains selected from the group consisting of the PIT domain, the central domain, the PYK2 binding domain, the calcium binding domain and the nucleotide binding domain.

13. An isolated or purified rdgB polypeptide comprising the full length sequence set forth in SEQ ID NO: 6 except that it lacks at least one, but not more than two, of the domains selected from the group consisting of the PIT domain, the central domain, the PYK2 binding domain, the calcium binding domain and the nucleotide binding domain.

* * * * *